United States Patent
Kvam et al.

(10) Patent No.: US 11,142,758 B2
(45) Date of Patent: *Oct. 12, 2021

(54) METHOD AND DEVICE FOR COLLECTION AND AMPLIFICATION OF CIRCULATING NUCLEIC ACIDS

(71) Applicant: Global Life Sciences Solutions Operations UK Ltd, Sheffield (GB)

(72) Inventors: Erik Leeming Kvam, Niskayuna, NY (US); John Richard Nelson, Niskayuna, NY (US); Gregory Andrew Grossmann, Niskayuna, NY (US); Ryan Charles Heller, Niskayuna, NY (US); Erin Jean Finehout, Broomfield, CO (US); Christopher Michael Puleo, Niskayuna, NY (US); William Patrick Waters, Niskayuna, NY (US)

(73) Assignee: Global Life Sciences Solutions Operations UK Ltd, Sheffield (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/463,943

(22) Filed: Mar. 20, 2017

(65) Prior Publication Data

US 2017/0211059 A1 Jul. 27, 2017

Related U.S. Application Data

(63) Continuation of application No. 13/952,173, filed on Jul. 26, 2013, now Pat. No. 9,644,232.

(51) Int. Cl.
| | | |
|---|---|---|
| *C12Q 1/68* | (2018.01) | |
| *C12N 15/10* | (2006.01) | |
| *B01L 3/00* | (2006.01) | |
| *C12Q 1/6844* | (2018.01) | |
| *B01L 7/00* | (2006.01) | |

(52) U.S. Cl.
CPC ........ *C12N 15/1017* (2013.01); *B01L 3/5023* (2013.01); *B01L 7/52* (2013.01); *C12Q 1/68* (2013.01); *C12Q 1/6844* (2013.01); *B01L 2300/0681* (2013.01); *B01L 2300/0825* (2013.01)

(58) Field of Classification Search
None
See application file for complete search history.

(56) References Cited

U.S. PATENT DOCUMENTS

| | | | |
|---|---|---|---|
| 6,156,504 A | 12/2000 | Gocke et al. | |
| 6,329,179 B1 | 12/2001 | Kopreski | |
| 6,511,805 B1 | 1/2003 | Gocke et al. | |
| 6,521,409 B1 | 2/2003 | Gocke et al. | |
| 6,607,898 B1 | 8/2003 | Kopreski et al. | |
| 6,630,301 B1 | 10/2003 | Gocke et al. | |
| 6,759,217 B2 | 7/2004 | Kopreski | |
| 6,794,135 B1 | 9/2004 | Kopreski et al. | |
| 6,916,634 B2 | 7/2005 | Kopreski | |
| 6,939,671 B2 | 9/2005 | Kopreski | |
| 6,939,675 B2 | 9/2005 | Gocke et al. | |
| 7,183,053 B2 | 2/2007 | Gocke et al. | |
| 7,208,275 B2 | 4/2007 | Gocke et al. | |
| 7,282,335 B2 | 10/2007 | Gocke et al. | |
| 7,288,380 B1 | 10/2007 | Gocke et al. | |
| 7,387,874 B2 | 6/2008 | Gocke et al. | |
| 7,399,592 B2 | 7/2008 | Gocke et al. | |
| 7,410,764 B2 | 8/2008 | Gocke et al. | |
| 7,569,349 B2 | 8/2009 | Gocke et al. | |
| 7,569,350 B2 | 8/2009 | Gocke et al. | |
| 7,709,233 B2 | 5/2010 | Kopreski | |
| 7,767,422 B2 | 8/2010 | Kopreski et al. | |
| 7,767,423 B2 | 8/2010 | Kopreski | |
| 7,785,842 B2 | 8/2010 | Kopreski | |
| 7,790,395 B2 | 9/2010 | Gocke et al. | |
| 7,910,336 B2 | 3/2011 | Kopreski et al. | |
| 7,923,551 B2 | 4/2011 | Lee et al. | |
| 7,932,061 B2 | 4/2011 | Kopreski | |
| 7,935,484 B2 | 5/2011 | Gocke et al. | |
| 7,935,487 B2 | 5/2011 | Gocke et al. | |
| 7,968,317 B2 | 6/2011 | Kopreski et al. | |

(Continued)

FOREIGN PATENT DOCUMENTS

| | | |
|---|---|---|
| JP | H11-155597 A | 6/1999 |
| JP | 2004-526432 A | 9/2004 |

(Continued)

OTHER PUBLICATIONS

Jorgez et al. (Reproductive BioMedicine Online, 2008, 17(5), p. 716-721) (Year: 2008).*
Li et al. (Rapid Commun Mass Spectrom., 2012, 26:1208-1212) (Year: 2012).*
Li, J., et al., "Whole Genome Amplification of Plasma-Circulating DNA Enables Expanded Screening for Allelic Imbalance in Plasma," Journal of Molecular Diagnostics, vol. 8, Issue 1, pp. 22-30 (2006).
First Office Action and Search issued in connection with corresponding CN Application No. 201480042256.7 dated Sep. 5, 2018.
Machine Translation and Notification of reasons for refusal issued in connection with corresponding JP Application No. 2016-530047 dated Jun. 26, 2018.
Australian Examination Report for AU Application No. 2014293096 dated Oct. 1, 2019 (3 pages).

(Continued)

*Primary Examiner* — Stephanie K Mummert
(74) *Attorney, Agent, or Firm* — Eversheds Sutherland (US) LLP

(57) ABSTRACT

Provided herein are methods for the collection and amplification of circulating nucleic acids from a non-celluar fraction of a biological sample. Circulating nucleic acids are extracted from the non-cellular fraction and are circularized to generate single-stranded nucleic acid circles, which are then subsequently amplified by rolling circular amplification using random primers to produce an amplified library. Devices for the collection of a non-cellular fraction from a biological sample are also provided. The device includes a filtration membrane and a dry solid matrix, which is in direct contact with the filtration membrane.

20 Claims, 14 Drawing Sheets

(56) References Cited

U.S. PATENT DOCUMENTS

| | | |
|---|---|---|
| 7,972,817 B2 | 7/2011 | Kopreski |
| 8,030,031 B2 | 10/2011 | Kopreski |
| 8,043,835 B1 | 10/2011 | Kopreski |
| 8,048,629 B2 | 11/2011 | Gocke et al. |
| 8,163,524 B2 | 4/2012 | Kopreski |
| 2006/0016747 A1* | 1/2006 | Sakaino ............. B01D 39/2017 210/450 |
| 2006/0240451 A1 | 10/2006 | Jendrisak et al. |
| 2012/0024788 A1* | 2/2012 | Kelso .................... B01L 3/5023 210/651 |
| 2014/0017672 A1* | 1/2014 | Holmberg ............. G01N 1/405 435/5 |

FOREIGN PATENT DOCUMENTS

| | | | | |
|---|---|---|---|---|
| JP | 2005-531751 A | 10/2005 | | |
| WO | WO-2008045505 A2 * | 4/2008 | ........... | C12N 15/101 |
| WO | 2008/084219 A1 | 7/2008 | | |
| WO | WO-2008084219 A1 * | 7/2008 | ........... | C12Q 1/6886 |
| WO | 2012/135815 A2 | 10/2012 | | |

OTHER PUBLICATIONS

Korean Office Action for KR Application No. 10-2016-7001767 dated Dec. 23, 2020 (8 pages with English translation).
Chinese Office Action for CN Application No. 201480042256.7 dated May 27, 2020 (19 pages with English translation).

* cited by examiner

| Locus | Amplicon size (bp) | Genomic DNA | Plasma DNA | CircLigase II - treated plasma DNA |
|---|---|---|---|---|
| mini CSF1PO | 89-129 | 22.26 | X | 25.55 |
| mini TH01 | 51-98 | 23.43 | X | 25.24 |
| mini TPOX | 65-101 | 24.62 | X | 23.92 |
| mini vWA | 88-148 | 21.29 | X | 20.66 |
| mini D5S818 | 81-117 | 22.14 | X | 26.19 |
| mini D7S820 | 136-176 | 23.46 | X | 27.11 |
| mini D8S1129 | 86-134 | 22.72 | X | 20.26 |
| mini D13S317 | 88-132 | 23.03 | 28.73 | 25.24 |
| mini D16S539 | 88-121 | 20.74 | 20.40 | 20.83 |
| mini D18S51 | 113-193 | 23.84 | X | X |
| Amelogenin | 106, 112 | 20.72 | 29.67 | 22.27 |
| D3S1358 | 99-147 | 20.13 | 20.77 | 20.85 |
| Total | | 12/12 loci | 4/12 loci | 11/12 loci |

FIG. 11

METHOD AND DEVICE FOR COLLECTION AND AMPLIFICATION OF CIRCULATING NUCLEIC ACIDS

CROSS-REFERENCE TO RELATED APPLICATIONS

This application is a continuation of U.S. patent application Ser. No. 13/952,173, filed Jul. 26, 2013, the entire disclosure of which is hereby incorporated by reference in its entirety.

BACKGROUND

This application relates generally to collection and amplification of circulating nucleic acids (CNAs) from a biological sample. More particularly, the application relates to separation, collection, amplification and further detection of circulating nucleic acids from the biological sample.

Circulating nucleic acids are released from a variety of tissues and are accumulated in bodily fluids. A variety of intact and/or fragmented nucleic acids have been identified in CNAs, including mRNA, miRNA, mitochondrial DNA, genomic DNA, and retrotransposons. CNAs are ideally suited for early detection of diseases as well as prognostic and theranostic applications. The diagnostic potential of CNAs has been demonstrated over a wide spectrum of diseases, including tumorigenesis, inflammation, myocardial infarction, autoimmune disorders and pregnancy-associated complications.

Circulating nucleic acids may be detected using minimally invasive methods that sample bodily fluids. However, CNAs are present in very low abundance in the bodily fluids. Hence, analysis of CNAs generally often requires collection and processing of large volumes (milliliters or liters) of bodily fluids. However, many times, only very small amounts of bodily fluid sample (microliters) may be available for analysis, especially in the fields of in vitro diagnostics, pathology, and forensics. Moreover, large-volume sample collection often leads to significant set-up costs, transportation/handling costs and sample artifacts. Additionally, since CNAs are present outside of cells in bodily fluids, this circulating pool of nucleic acids can be gradually swamped out by intra-cellular DNAs or RNAs that are released through lysis of resident cells in bodily fluids. This swamping out or contamination may be a multi-parameter function of time, temperature, type of treatment for stabilization, and separation forces used for isolation of bodily fluids. These pre-analytical variables can produce undesirable genomic contamination from the resident cells that are present in the bodily fluid. For example, in whole blood samples, DNAs or RNAs may be released into plasma or serum from blood cells during storage and processing. This may interfere with the analysis of extra-cellular, circulating nucleic acids that are present in the plasma or serum. Genomic contamination of circulating nucleic acid pools may be reduced by maintaining the blood sample at 4° C. and processing the sample within 2 hours. However, such conditions are often not feasible and/or cost-effective for many applications.

Whole-genome amplification may be used expand the natural pool of circulating nucleic acids. However, prior attempts at whole-genome amplification of CNAs using multiple displacement amplification (MDA) techniques have highlighted unique challenges that are associated with the poor quality and low quantity of CNAs in the bodily fluids. Generally, by nature, CNAs are highly fragmented due to their origin from apoptotic/necrotic cells. The nucleic acid fragmentation pattern of CNAs is not ideal for conventional whole-genome amplification and thus leads to allelic drop-out and/or sequence-biased amplification patterns. Additionally, many of the conventional whole-genome amplification techniques require nanogram quantities of input nucleic acids. Hence, CNAs must be purified from large volumes of non-cellular fraction to meet these template concentration demands. In view of the above, there is a critical need for technologies that streamline the separation, collection, stabilization and/or amplification of circulating nucleic acids from a biological sample, particularly when analyzing small sample volumes containing picogram quantities of CNAs.

BRIEF DESCRIPTION OF THE INVENTION

The present invention is directed at collection and subsequent amplification of CNAs from a biological sample.

One aspect of the invention relates to a method for amplification of circulating nucleic acids that are present in a non-cellular fraction of a biological sample. The method includes the steps of filtering the biological sample to separate the non-cellular fraction from intact cells, collecting the separated, non-cellular fraction onto a dry solid matrix, and extracting CNAs from the collected, non-cellular fraction. The method further includes the steps of circularizing the extracted CNAs to form single-stranded nucleic acid circles, and amplifying the single-stranded nucleic acid circles by random-primed rolling circular amplification to form an amplified, CNA product. If CNAs are in double-stranded form, the method also includes the step of denaturing the double-stranded CNAs to a single-stranded form prior to the intra-molecular ligation reaction for making single-stranded nucleic acid circles. The circularization of linear single-stranded CNAs may be achieved by a ligase that is capable of intra-molecular ligation of single-stranded nucleic acids.

Another aspect of the invention relates to a method for processing whole blood at a point-of-collection to collect plasma or serum that contains circulating nucleic acids. The method includes the steps of filtering the whole blood to separate the plasma or serum from the whole blood at the point-of-collection, collecting the separated plasma or serum on to a dry solid matrix and drying the collected plasma on to the solid matrix. The solid matrix is devoid of any detergent.

Another aspect of the invention relates to a method for detection of CNAs from a dried sample of plasma or serum. The method includes steps of extracting the CNAs from the dried plasma or serum, performing a whole genome amplification of the extracted circulating nucleic acids to form an amplified, circulating nucleic acid (CNA) product, and detecting a specific circulating nucleic acid sequence in the amplified, CNA product. The whole genome amplification is performed by first circularizing the extracted CNAs using a ligase that is capable of intra-molecular ligation of single-stranded nucleic acids to form single-stranded nucleic acid circles, and amplifying the single-stranded nucleic acid circles by rolling circular amplification employing random primers. If the CNAs are in double-stranded forms, the method also includes the step of denaturing the double-stranded CNAs to its single-stranded form prior to the intra-molecular ligation reaction.

Another aspect of the invention relates to a device for collecting a non-cellular fraction of a biological sample that comprises circulating nucleic acids. The device comprises a filtration membrane configured to separate the non-cellular fraction of the biological sample from intact cells, and a dry solid matrix configured to collect the separated, non-cellular fraction. The filtration membrane and the solid matrix are configured to establish a direct contact between them. Further, the solid matrix is devoid of any detergent.

DRAWINGS

These and other features, aspects, and advantages of the described invention will become better understood when the following detailed description is read with reference to the accompanying drawings in which like characters represent like parts throughout the drawings, wherein:

FIG. 11 illustrates the effectiveness of ligase-assisted whole-genome amplification for sensitive and balanced DNA amplification of twelve different CODIS loci.

DETAILED DESCRIPTION

Figure 1:
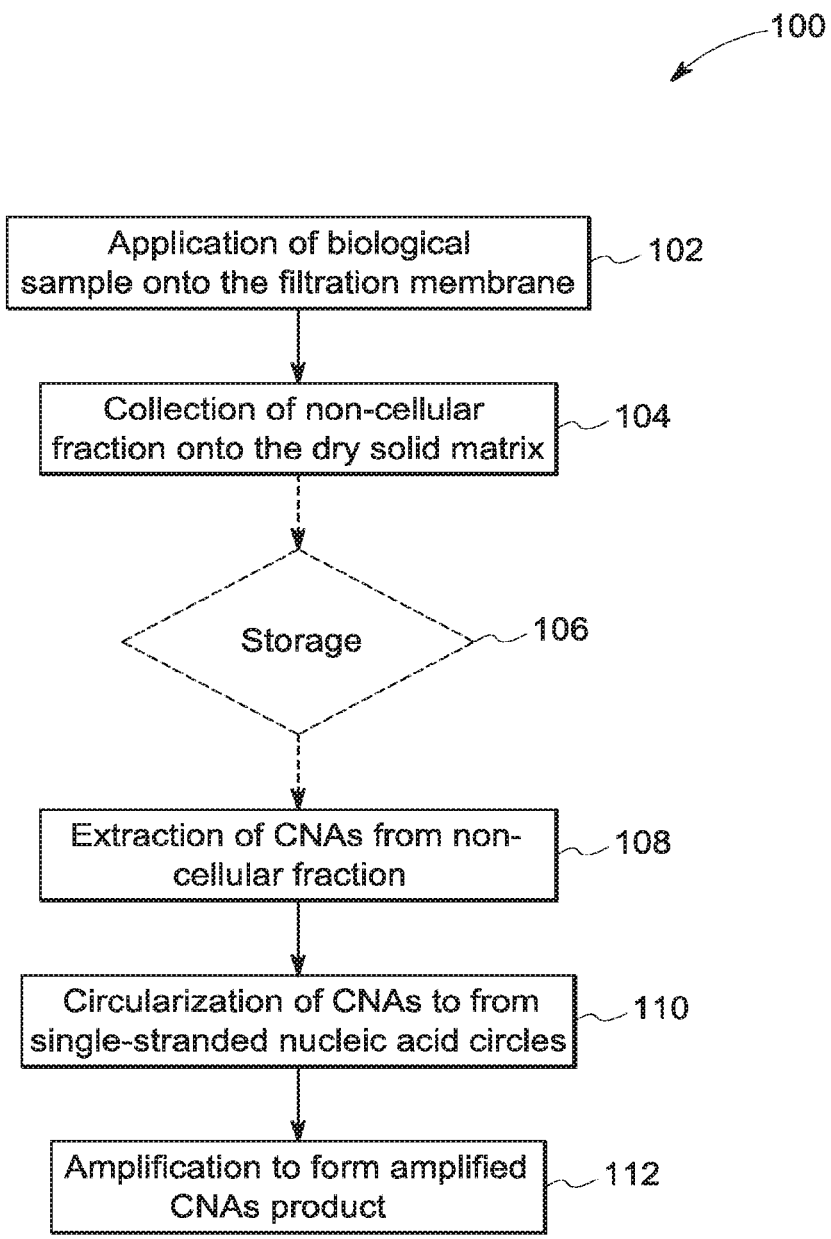
FIG. 1 depicts a flow diagram illustrating an embodiment of the method of the invention.

The following detailed description is exemplary and is not intended to limit the claimed invention or uses of the claimed invention. Furthermore, there is no intention to be limited by any theory presented in the preceding background of the claimed invention or the following detailed description.

In the following specification and the claims which follow, the singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." In some instances, the approximating language may correspond to the precision of an instrument for measuring the value.

As used herein, the term "biological sample" refers to any type of biological fluid obtained from a biological subject of eukaryotic origin. Non-limiting examples of biological samples include whole blood, urine, saliva, sweat, tears, amniotic fluid, breast milk, nasal wash or bronchoalveolar lavage fluids. In some embodiments, the biological sample is of mammalian (e.g., rat, mouse, cow, dog, donkey, guinea pig, or rabbit) origin. In certain embodiments, the biological sample is of human origin.

As used herein, the term "intact cell" refers to non-disrupted cells that may be present in a biological sample (i.e., a biological fluid). Since intact cells are not disrupted, no nucleic acids and/or nucleic acid fragments are released from inside of an intact cell into non-cellular fractions of the biological sample. The intact cells may include resident eukaryotic cells (e.g., blood cells in a whole blood) and/or circulating cells (e.g., circulating tumor cells in a whole blood). In some embodiments, the intact cells may include other pathogenic cells (e.g., bacterial or viral cells) that may be present in the biological sample.

As used herein, the term "non-cellular fraction" refers to the component of a biological sample that is devoid of intact cells. For example, the non-cellular fraction of whole blood comprises plasma and serum, which are devoid of intact blood cells (e.g. white blood cells, red blood cells and platelets). Based on the pore size of the filtration membrane used for the generation of non-cellular fraction, the non-cellular fraction may be devoid of eukaryotic cells, prokaryotic cells and/or viral cell particles.

As used herein, the term "circulating nucleic acid" or "CNA" refers to cell-free nucleic acids that are found in the non-cellular fraction of a biological sample. The cell-free nucleic acids are those nucleic acids that are not restricted to an inside cellular compartment (e.g., nucleus, mitochondria etc.) of a biological cell. The circulating nucleic acid may be a deoxyribonucleic acid (DNA) or a ribonucleic acid (RNA).

As used herein, the term "direct contact" refers to a contiguous contact between two components. The direct contact between two components is achieved by placing the two components such that they directly touch each other.

As used herein, the terms "ssLigase" or "single-strand specific ligase" refers to a ligase that is capable of intra-molecular ligation of single-stranded nucleic acids.

In some embodiments, the invention is directed to a method for collecting and amplifying CNAs from biological samples. Elevated concentrations of CNAs are often found in the non-cellular fraction of a biological sample that is collected from patients with several pathologies when compared with healthy individuals, indicating their potential as disease biomarkers. For example, tumor-derived circulating nucleic acids that are found in the plasma or serum fraction of whole blood may be used to detect, monitor, or evaluate cancer and pre-malignant states. Methods for amplification of CNAs in the non-cellular fraction of biological sample may therefore aid in the detection, diagnosis, monitoring, treatment, and/or evaluation of diseases such as neoplastic diseases, inflammation, myocardial infarction, autoimmune disorders, transplanted organ/tissue rejection, pregnancy-associated complications, and so forth. The neoplastic diseases may include, but not limited to, early cancer, premalignant states or advanced cancer.

Some embodiments of the invention relate to methods and devices for separation and collection of non-cellular fraction of a biological sample that contains circulating nucleic acids. After separating and collecting the non-cellular fraction from intact cells, the method further includes the steps of extracting circulating nucleic acids from the non-cellular fraction and amplifying these nucleic acids to create an amplified CNA library. The method and device described herein provide a simplified and integrated solution for CNA collection and amplification. The method and device may be suitable for use at a point-of-collection, and may be employed with low sample volumes (e.g., less than about 150 µL). Thus devices and the associated methods described herein reduce sample processing time and minimize sample artifacts related to genomic DNA or RNA contamination, and help increase the sensitivity of CNA amplification and/or detection.

In some embodiments, CNAs may be a tumor-derived circulating nucleic acid. In some other embodiments, CNAs may be derived from a fetus, a donated organ after implantation, a transplanted cell, a transplanted tissue, or a diseased state. In some embodiments, the circulating nucleic acids comprise circulating DNA or a circulating RNA. The circulating DNAs may include, but not limited to, a tumor-derived DNA, a fetus-derived DNA, a donated organ-derived DNA, a transplant cell-derived DNA, a transplanted tissue-derived DNA or a combination thereof.

One aspect of the invention relates to a method for amplification of circulating nucleic acids that are present in the non-cellular fraction of a biological sample. The method comprises the steps of filtering the biological sample to separate the non-cellular fraction from intact cells, collecting the separated, non-cellular fraction onto a dry solid matrix and extracting the CNAs from the collected, non-cellular fraction. The method further includes the steps of circularizing the extracted circulating nucleic acids by using a single-strand-specific ligase to form single-stranded nucleic acid circles, and amplifying the single-stranded nucleic acid circles by random-primed rolling circular amplification to form an amplified, CNA product. In some embodiments, a method for amplification and detection of a tumor-derived circulating DNA in the non-cellular fraction of a biological sample is provided.

FIG. 1 represents a flow diagram illustrating an embodiment of the invention. The biological sample is applied on to a device that comprises a filtration membrane membrane configured to separate the non-cellular fraction from intact cells, and a dry solid matrix configured to collect the separated non-cellular fraction. As shown in FIG. 1, the biological sample is applied on to the filtration membrane (102). Upon filtration, intact cells of the biological sample are retained on the upstream side/surface of filtration membrane and the non-cellular fraction is collected onto a dry solid matrix (104), which may be located either on the downstream side (in a lateral flow device) or on the downside surface (in a vertical flow device). The dry solid matrix containing the non-cellular fraction may then be stored (106) or may be directly used for extraction of circulating nucleic acids (108). The extracted circulating nucleic acids are then subsequently circularized by a ligase that is capable of intra-molecular ligation of single-stranded nucleic acids to form single-stranded nucleic acid circles (110). In some embodiments, the method further comprises drying the collected non-cellular fraction to a substantially dry state prior to extraction. If the CNAs are in the double-stranded form, prior denaturation of the circulating nucleic acids may be necessary before the ligation reaction. The single-stranded nucleic acid circles are then subsequently amplified by a random-primed, rolling circular amplification to form an amplified, CNA product.

Figure 2:
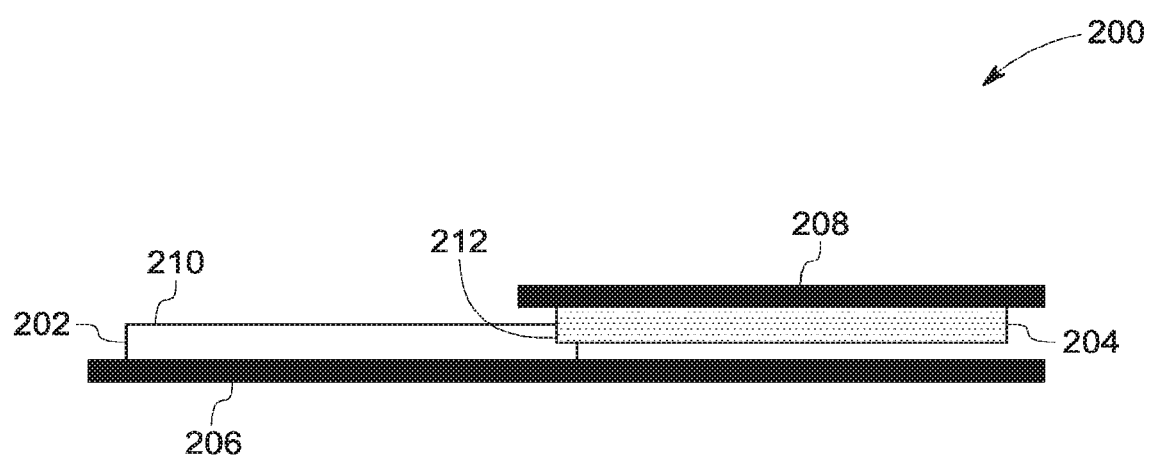
FIG. 2 depicts a schematic representation of a lateral flow device for the separation and collection of non-cellular fraction of a biological sample.

FIG. 2 depicts a schematic representation of one embodiment of a device that may be used for separating the non-cellular fraction of a biological sample. The filtration membrane (202) has a sample application zone (210) and a transfer zone (212). Filtration membrane is in direct contact with a solid matrix (204) via the transfer zone (212). The filtration step includes providing a biological sample at the sample application zone of the filtration membrane and passing the biological sample through the filtration membrane. The filtration membrane has a plurality of pores. Once the biological sample passes through the filtration membrane, resident intact cells within the biological sample are retained by the filtration membrane, mostly at the sample application zone (210) itself, and the non-cellular fraction are passed through the pores to reach the transfer zone (212) and gets transferred and collected onto the dry solid matrix. In some embodiments, a filtration membrane having pore size in the range of about 0.01 micron to about 5 micron may be employed. In some other embodiments, pore size of the filtration membrane may vary between about 0.22 micron to about 2 micron. In one example embodiment, the filtration membrane has a pore size between about 1 micron to about 2 micron. When a filtration membrane of 1 micron pore size is used, any other circulating eukaryotic cells and/or pathogenic cells having diameters greater than 1 micron will be retained in the filtration membrane and so will not reach the dry solid matrix upon filtration.

In some embodiments, the non-cellular fraction may be filtered out from the biological sample at the point-of-collection itself. Filtration may be performed without any prior pre-treatment of the biological sample. Further filtration may be performed in absence of any stabilizing reagent. After filtration, the separated, non-cellular fraction may be collected onto a dry solid matrix by means of physical interaction. The non-cellular fraction may be collected on to dry solid matrix by means of adsorption or absorption.

Filtration membrane may be made from a variety of materials. The materials used to form the filtration membrane may be a natural material, a synthetic material, or a naturally occurring material that is synthetically modified. Suitable materials that may be used to make the filtration membrane include, but are not limited to, glass fiber, polyvinyl alcohol-bound glass fiber, polyethersulfone, polypropylene, polyvinylidene fluoride, polycarbonate, cellulose acetate, nitrocellulose, hydrophilic expanded poly(tetrafluoroethylene), anodic aluminum oxide, track-etched polycarbonate, electrospun nanofibers or polyvinylpyrrolidone. In one example, the filtration membrane is formed from polyvinyl alcohol-bound glass fiber filter (MF1™ membrane, GE Healthcare). In another example, filtration membrane is formed from asymmetric polyethersulfone (Vivid™, Pall Corporation). In some embodiments, filtration membrane may be formed by a combination of two or more different polymers. For example, filtration membrane may be formed by a combination of polyethersulfone and polyvinylpyrrolidone (Primecare™, iPOC).

The non-cellular fraction that is collected on to the dry solid matrix upon filtration may then be dried to a substantially dry state and stored for later analysis. The term "substantially dry state" as used herein refers to conditions wherein the dried sample contain less than about 10% (wt/wt) water content. In some embodiments, the sample may be dried such that it contains less than about 5% water. In some other embodiments, the sample may be dried such that it contains less than about 2% water. In this way, CNAs that may be present in the non-cellular fraction of a biological sample may be stored in a dried form which is suitable for later subsequent analysis. The dried non-cellular fraction may be stored for long periods, for example, for at least 24 hours, for at least 7 days, for at least 30 days, for at least 90 days, for at least 180 days, for at least one year, or for at least 10 years. In one embodiment, non-cellular fraction is stored on the dry solid matrix for at least 30 minutes. Typically, samples are stored at temperatures ranging from −80° C. to 40° C. In addition, samples may be optionally stored under dry or desiccated conditions or under inert atmospheres. Drying may be done by air-drying under ambient condition or by vacuum-assisted evaporation. In some embodiments, the non-cellular fraction is dried under ambient conditions by normal evaporation and maintained in a low-humidity environment. The removal of water from the collected non-cellular fraction aids in stabilizing the circulating nucleic acids that are present in the non-cellular fraction.

A dry solid matrix suitable for this purpose includes, but is not limited to, a natural material, a synthetic material, or a naturally occurring material that is synthetically modified. Suitable materials that can act as dry solid matrix include, but are not limited to, cellulose, cellulose acetate, nitrocellulose, carboxymethylcellulose, quartz fiber, hydrophilic polymers, polytetrafluroethylene, fiberglass and porous ceramics. Hydrophilic polymers may be polyester, polyamide or carbohydrate polymers. In some embodiments, the dry solid matrix is comprised of cellulose. The cellulose-based dry solid matrix is devoid of any detergent. In some embodiments, cellulose-based dry solid matrix may not be impregnated with any reagent. In other embodiments, cellulose-based dry solid matrix may be impregnated with a chaotropic salt. Examples of chaotropic salt include, but are not limited to, guanidine thiocyanate, guanidine chloride, guanidine hydrochloride, guanidine isothiocyanate, sodium thiocyanate, and sodium iodide. In some embodiments, the cellulose-based dry solid matrix is FTA™ Elute (GE Healthcare).

After collection of non-cellular fraction onto the dry solid matrix, CNAs are extracted from this collected non-cellular fraction. The extraction may be performed using any of the conventional nucleic acid extraction method. Non-limiting examples of extraction methods that may be used include, but are not limited to, electroelution, gelatin extraction, silica or glass bead extraction, guanidine-thiocyanate-phenol solution extraction, guanidinium thiocyanate acid-based extraction, centrifugation through sodium iodide or similar gradient, or phenol-chloroform-based extraction. The extraction step helps to remove impurities such as proteins and concentrates the circulating nucleic acids. Extracted circulating nucleic acids may be inspected using methods such as agarose gel electrophoresis, spectrophotometry, fluorometry, or liquid chromatography.

The extracted CNAs are then converted to single-stranded nucleic acid circles via an intra-molecular ligation reaction after extraction. The CNAs may either be in a double-stranded or in a single-stranded form. Furthermore, CNAs may often be highly fragmented. The double-stranded CNAs are denatured to a single-stranded form prior to the intra-molecular ligation reaction. This denaturation of double-stranded nucleic acids to single-stranded form may be achieved by using any of the art-recognized methods. For example, the double-stranded nucleic acid may be thermally denatured, chemically denatured, or both thermally and chemically denatured. The double-stranded nucleic acid may be chemically denatured using a denaturant (e.g., glycerol, ethylene glycol, formamide, or a combination thereof) that reduces the melting temperature of double-stranded nucleic acid. The denaturant may reduce the melting temperature by 5° C. to 6° C. for every 10% (vol./vol.) of the denaturant added to the reaction mixture. The denaturant or combination of denaturants (e.g., 10% glycerol and 6-7% ethylene glycol) may comprise 1%, 5%, 10%, 15%, 20%, or 25% of reaction mixture (vol./vol.). For example, salts that reduce hybridization stringency may be included in the reaction buffers at low concentrations to chemically denature the double-stranded circulating DNAs at low temperatures. The double-stranded circulating DNA may also be thermally denatured by heating at 95° C. to form single-stranded DNA (ssDNA). After the denaturing step, the generated single-stranded nucleic acids may be treated with a single-strand specific ligase that is capable of intra-molecular ligation of single-stranded nucleic acid substrates to form single-stranded nucleic acid circles.

Intra-molecular ligation of single-stranded circulating nucleic acids may be performed in the presence or absence of a template by employing any of the conventional methods used for intra-molecular ligation of single-stranded nucleic acids. For example, conversion of linear, single-stranded DNA molecules to single-stranded DNA circles is conventionally performed via a template-dependent intra-molecular ligation reaction using a ligation enzyme such as T4 RNA ligase. However, template-dependent intra-molecular ligation of single-stranded DNA or single-stranded RNA has met only with limited success, particularly when the circularization of single-stranded DNA molecules is to be performed in a population of single-stranded DNA molecules of unknown sequence and/or size. Even though bacteriophage T4RNA ligase I exhibits a template-independent intra-molecular ligation activity, this activity is far too low and inefficient for practical use in generating circular single-stranded DNA molecules from linear, single-stranded DNA molecules. In some embodiments, intra-molecular ligation of the extracted single-stranded circulating nucleic acids is performed in the absence of any template. For example, single-stranded DNA sequences that even are shorter than 500 nucleotides may be circularized using template-independent intra-molecular ligation. Further, no prior knowledge of the target sequence is needed to create DNA circles when the ligation of the single stranded DNA (ssDNA) is performed in a template-independent manner.

In some embodiments, conversion of the linear single-stranded circulating nucleic acids to single-stranded nucleic acid circles is performed with a thermostable RNA ligase that has good template-independent, intra-molecular ligation activity for linear single-stranded DNA and/or single-stranded RNA substrates that have 5' phosphoryl and 3' hydroxyl groups. Suitable ligases that may be used for template-independent intra-molecular ligation of extracted single-stranded circulating nucleic acids include, but are not limited to, TS2126 RNA ligase, T4 DNA ligase, T3 DNA ligase or *E. coli* DNA ligase. For example, TS2126 RNA ligase derived from the *Thermus* bacteriophage TS2126 that infects the thermophilic *bacterium, Thermus scotoductus*, may be employed for template-independent circularization of the linear circulating ssDNA to generate circular, single-stranded DNA. TS2126 RNA ligase is more thermostable (stable up to about 75° C.) than many of the mesophilic RNA ligases such as the T4 RNA ligase. As a result, TS2126 RNA ligase may be used at higher temperatures, which further reduce undesirable secondary structures of ssDNA. HEPES buffer having a pH of 8.0 may be used for increasing the efficiency of TS2126 RNA ligase-mediated intra-molecular ligation. The circularization of extracted single-stranded circulating DNA may also be achieved using a ligase other than TS2126 RNA ligase or by employing any other enzyme having DNA joining activity such as topoisomerase. In some embodiments, circularization of ssDNA molecule may be achieved by an RNA ligase 1 derived from thermophilic archeabacteria, *Methanobacterium thermoautotrophicum* (Mth1) that has high template-independent ligase activity in circularizing linear, fragmented single stranded DNA molecules.

The single-stranded nucleic acid circles may then be amplified under isothermal conditions by employing rolling circle amplification (RCA) methods. The amplification of single-stranded nucleic acid circles may be performed in the same reaction vessel in which the intra-molecular ligation is performed. Isolation or purification of single-stranded nucleic acid circles and/or removal of the ligase may not be necessary prior to the amplification reaction. In some embodiments, the entire process of single-stranded nucleic acid ligation and amplification may be performed in a single tube without any intermediate purification or isolation steps.

In some embodiments, the method further comprises detecting nucleic acids from the amplified, circulating nucleic acid product. Detection of nucleic acids from the amplified, circulating nucleic acid product is done by methods known in the art. Various methods of detection of amplified product includes, but are not limited to, PCR, RT-PCR, qPCR, RT-qPCR, restriction enzyme-based methods, agarose gel electrophoresis, ELISA detection methods, electrochemiluminescence, high performance liquid chromatography, Southern blot hybridization, Northern blot hybridization, or reverse dot blot methods. In one embodiment, the detection is performed by quantitative PCR using specific primers that amplify a specified target within the circulating nucleic acid amplification product. The detection may be performed to identify the presence, absence and/or quantity of a specific circulating nucleic acid sequence in the amplified, circulating nucleic acid product.

The whole genome amplification methods disclosed herein improve amplification sensitivity, reduce sequence dropout and allow more balanced amplification. The described methods are advantageous especially when limited quantities of biological sample are available. In some embodiments, a non-cellular fraction is isolated from a total biological sample volume of about 10 µL to about 500 µL. Further, both the circularization and amplification reactions may be performed in a single reaction vessel without any intermediated purification or isolation steps thereby reducing the chances of contamination and simplifying the amplification workflow.

In some embodiments, whole genome amplification of fragmented, circulating DNAs via multiple displacement amplification (MDA) are provided. The circulating DNAs, by its nature of origin, are often highly fragmented. Furthermore, the amount of circulating DNAs in the non-cellular fraction of a biological sample is generally very low. Conventional methods of MDA, when attempted on linear fragmented DNA, result in decreased amplification speed, significant sequence dropout and lead to highly sequence-biased amplification. To overcome these limitations, after extraction of the circulating DNAs from the dry solid matrix, the fragmented double-stranded circulating DNAs are first converted to their single-stranded form. The single-stranded circulating DNAs are then converted to single-stranded, DNA circles via a template-independent intra-molecular ligation reaction, thereby eliminating the problematic DNA ends. After circularization of the fragmented single-stranded circulating DNA, MDA is performed on the circularized DNA.

The MDA reaction of the extracted circulating DNAs may be performed under isothermal conditions via employing rolling circle amplification (RCA) methods. For amplification of single-stranded DNA circles, amplification reagents including a DNA polymerase, primers and dNTPs may be added to the same reaction vessel where ligation is performed to produce an amplification reaction mixture to initiate an RCA reaction. The amplification reaction mixture may further include reagents such as single-stranded DNA binding proteins and/or suitable amplification reaction buffers. RCA may be performed by using any of the strand displacing DNA polymerases that are known in the art such as a Phi29 DNA polymerase. RCA may be performed using commercially available RCA amplification kits such as TempliPhi™ RCA kit (GE Healthcare). The TempliPhi™ rolling-circle amplification employs locked nucleic acid-containing random primers, which provide higher sensitivity and amplification balance. In some embodiments, random primers are used for the RCA reaction. The primer sequences comprising one or more nucleotide analogues (e.g., LNA nucleotides) may be used. In some embodiments, nuclease-resistant primers (e.g., primer sequences comprising phosphorothioate groups at appropriate positions) are employed for amplification reaction (e.g., NNNN*N*N, where *N represents a random nucleotide with a phosphorothioate linkage). In some embodiments, rolling circle amplification may be performed by contacting the single-stranded DNA circles with a primer solution comprising a random primer mixture to form a DNA template-primer complex; contacting the DNA template-primer complex with a DNA polymerase and deoxyribonucleoside triphosphates; and amplifying the DNA template. Since template-independent circularization of single-stranded DNA may be achieved on short sequences even at low concentrations, a more balanced DNA amplification with faster kinetics and improved sequence coverage may be achieved when ligase-assisted whole-genome amplification is employed for amplification of highly fragmented circulating DNAs (e.g., circulating DNAs that are present in whole blood).

Figure 7:
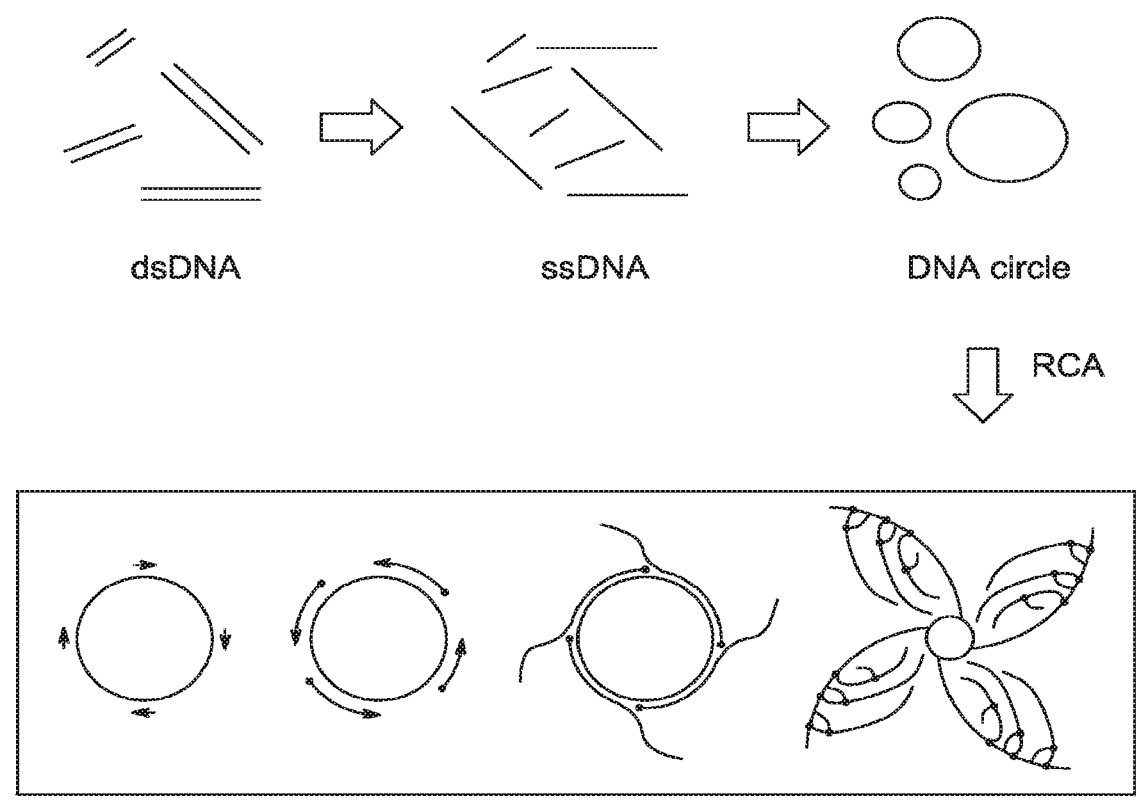
FIG. 7 illustrates a schematic representation of an embodiment of a ligase-assisted whole-genome amplification of a linear double stranded DNA.

FIG. 7 depicts a schematic representation of an embodiment of ligase-assisted whole-genome amplification of a fragmented double-stranded circulating DNA. The persistence length of double-stranded DNA is much higher (~150 bp) than single-stranded DNA, and its innate stiffness makes circularization of fragments less than 500 bp highly inefficient. Further, with small double-stranded fragmented DNA molecules of about 250 bp range, circularization is inefficient unless the ends are in proper alignment (~10.5 bp/turn). In contrast, the persistence length of the circularization of single-stranded fragmented DNA is very small, approximately 15 nucleotides, as compared to the double-stranded fragmented DNA. As depicted in FIG. 7, in ligase-assisted whole-genome amplification, fragmented double-stranded circulating DNA is first converted into single-stranded DNA circles. This may be achieved by incubating the fragmented double-stranded circulating DNA at 95° C. for sufficient period in order to denature the double stranded DNA into single strands. The fragmented single stranded circulating DNA is then treated with a DNA or RNA ligase that is capable of template-independent, intra-molecular ligation of single-stranded circulating DNA substrates to generate single-stranded DNA circles. Amplification reagents, including DNA polymerase, random primers, and dNTPs are then added to initiate a RCA reaction on the single-stranded DNA circles. This ligase-assisted whole-genome RCA amplification produces large quantities of DNA with reduced sequence dropout and amplification bias in contrast to the conventional whole-genome amplification methods. Therefore, it may be used to amplify and detect even highly fragmented circulating DNA. In some embodiments, the entire process of generation of the single-stranded DNA circles and its subsequent amplification by RCA is done in a single tube without any intervening purification steps.

Figure 13:
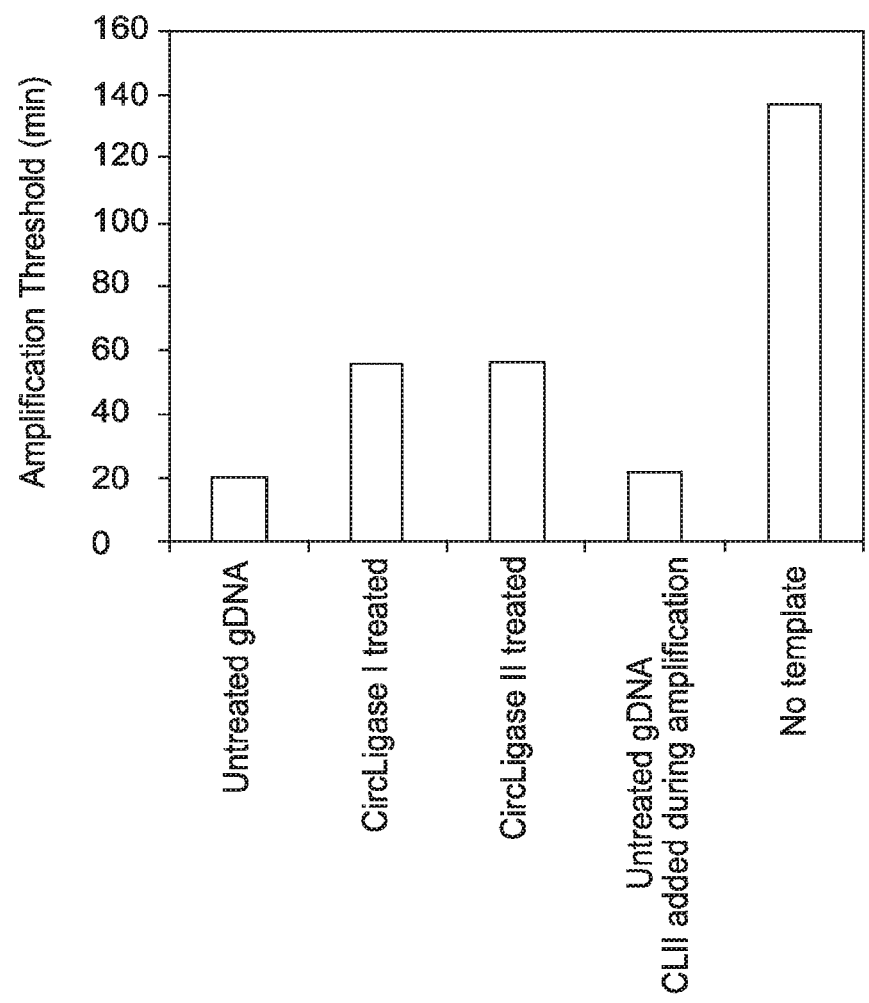
FIG. 13 illustrates the inhibition of amplification of high molecular weight genomic DNA in ligase-assisted whole-genome amplification.

Ligation-assisted whole-genome amplification methods provided herein, which comprise prior ligation of single-stranded circulating DNA fragments to DNA circles followed by rolling circle amplification, provides preferential amplification of fragmented CNA over high molecular weight genomic DNA. For example, plasma preparations comprising CNA may often be contaminated with genomic DNA that are released from blood cells during the purification process. Conventional methods of whole-genome amplification via MDA amplify both the circulating DNA and the genomic DNA. In contrast, when fragmented, CNA molecules are first circularized using TS2126 RNA ligase followed by amplification via RCA employing a Phi29 DNA polymerase, circulating DNAs were preferentially amplified over the high molecular weight genomic DNA. Such preferential amplification of fragmented circulating DNA over the genomic DNA is particularly suitable for diagnostic applications since diagnostically relevant DNA may be preferentially amplified for downstream analysis (FIG. 13). Further, ligase-assisted whole-genome amplification allows more robust amplification of fragmented DNA as compared to conventional MDA-based whole-genome amplification.

In some embodiments, sensitivity of circulating DNA amplification and detection in the non-cellular fraction of a biological sample may further be increased by phosphorylating the extracted circulating DNAs with a polynucleotide kinase (PNK) prior to the ssDNA ligation step and RCA. Intra-molecular ligation of DNA is not feasible unless the ssDNA template has a 5' phosphate group and a 3' hydroxyl group. A variety of conditions (e.g., DNase II enzymatic cleavage, and phosphatase activity in blood) may lead to the generation of circulating DNAs with non-ligatable DNA sequences having either 5' hydroxyl groups or 3' phosphate groups or both. The PNK treatment converts these non-ligatable DNA sequences to ligatable DNA sequences by phosphorylating the 5' end or dephosphorylating the 3' end. This improves the diversity of rolling-circle amplified CNA library. Upon incorporating the PNK step in the work flow, ligase-assisted whole-genome amplification methods presented herein could detect male circulating DNA in female whole blood when spiked at 1% levels (triplicate repeats, FIG. 14).

In one embodiment, a method for amplification and detection of circulating nucleic acids that are present in whole blood is provided. Whole blood comprises a cellular fraction (i.e. white blood cells, red blood cells and platelets) and a non-cellular fraction (e.g., plasma or serum). Circulating DNA is amplified from the non-cellular fraction of the whole blood (e.g., plasma or serum). In a preferred embodiment, plasma or serum is separated from a fingerstick volume of blood. The method comprises the steps of collecting the non-cellular fraction of the whole blood, extracting the circulating DNAs (mostly presented in its native double-stranded form) from the non-cellular fraction, denaturing the double-stranded circulating DNAs to generate single-stranded DNAs, circularizing the circulating single-stranded DNAs to generated single-stranded DNA circles, and amplifying the single-stranded DNA circles via rolling circle amplification to form an amplified circulating nucleic acid product. While filtering the whole blood using the device described herein, plasma or serum passes through the pores of filtration membrane and gets collected onto a dry solid matrix. The intact blood cells are retained by the filtration membrane. Plasma or serum may be separated from the whole blood sample by filtration in the absence of an anticoagulant. Therefore, no extra steps are required to maintain the integrity of the whole blood sample prior to filtration. In some embodiments, biological sample may be pre-treated with reagents like anticoagulant before filtration. The genomic contamination from intact blood cells may be minimized by filtering the whole blood at the point-of-collection. In one embodiment, the separated plasma or serum, containing CNAs, is adsorbed on to a dry solid matrix by passive wicking. In one embodiment, circulating DNAs are extracted from the plasma or serum previously collected onto a solid matrix using sodium iodide and alcohol (DNA Extractor SP™, Wako Chemical). In one example, the plasma is separated from less than 150 µL of whole blood.

It is often not possible to circularize double-stranded DNA that has a sequence length smaller than 150 bp, and it is very difficult to circularize double stranded DNA until the DNA is longer than 200 bp. In contrast, linear single stranded DNA molecules having a sequence length of 15 nucleotides or more are very efficiently circularized by a suitable ligase as long as the 5' end is phosphorylated and the 3' end is hydroxylated. The circularization of the single-stranded DNA to generate single-stranded DNA circle may be achieved by employing a ligase that is capable of template-independent intra-molecular ligation of single-stranded DNA. In some embodiments, the circularization of the single-stranded DNA molecules is performed by treating the single-stranded linear DNA with an RNA ligase such as CircLigase II™.

Another aspect of the invention relates to a method for processing whole blood at a point-of-collection itself to collect plasma or serum. The method comprises the steps of filtering the whole blood to separate the plasma or serum at the point of sample collection, collecting the separated plasma or serum on to a dry solid matrix, wherein the solid matrix is devoid of any detergent and drying the collected plasma or serum in the solid matrix. In some embodiments, filtration is done by using MF1™ membrane and collection is done using a cellulose-based solid matrix arranged laterally to MF1™ membrane. In other embodiments, Vivid™ or Primacare™ membrane and a Cellulose-based solid matrix are arranged vertically. In one example, either the whole blood or the filtration membrane is not pre-treated with any anticoagulant. In another example, blood and/or filtration membrane is pre-treated with an anticoagulant. In some embodiments, a cellulose matrix that is impregnated with a chaotropic salt may be used to collect the plasma or serum at the point-of-collection. Suitable chaotropic salts that may be employed includes, but not limited to, guanidine thiocyanate, sodium thiocyanate, potassium thiocyanate, or guanidine hydrochloride. The solid matrix that contains dried plasma or serum may be stored for longer periods, and the circulating nucleic acids may be extracted, amplified and detection from this dried plasma or serum at a later point in time.

In some aspects, a method for detecting circulating nucleic acids from a dried sample of plasma or serum is provided. The method comprises the steps of extracting the circulating nucleic acids from a dried plasma or serum sample, performing a whole genome amplification of the extracted circulating nucleic acids to generate an amplified circulating nucleic acid product and then detecting the presence, absence, or quantity of a specific circulating nucleic acid sequence within the amplified circulating nucleic acid product. Whole genome amplification of the extracted circulating nucleic acids may be achieved by first circularizing the extracted circulating nucleic acids by a single-stranded specific ligase to form single-stranded nucleic acid circles and amplifying the single stranded nucleic acid circles by random-primed rolling circular amplification to form the amplified circulating nucleic acids product. The detection of specific circulating nucleic acid sequences in the amplified library may be achieved by any of the conventional nucleic acid detection technologies. The method may further include the step of denaturing double-stranded CNAs to their single-stranded form prior to the intra-molecular ligation reaction by a single-strand specific ligase.

Another aspect of the invention relates to a device for collecting the non-cellular fraction of a biological sample, which contains the circulating nucleic acids. The device comprises a filtration membrane configured to separate the non-cellular fraction of the biological sample from intact cells, and a dry solid matrix configured to collect the separated non-cellular fraction. The solid matrix is devoid of any detergent and is in direct contact with the filtration membrane. The device may be a lateral flow device or a vertical flow device.

FIG. 2 depicts a schematic representation of a lateral flow device (200) as described in one embodiment of the invention. The lateral flow device contains a filtration membrane (202) and a dry solid matrix (204). The filtration membrane and the dry solid matrix are arranged laterally such that the non-cellular fraction of the biological sample passes through the filtration membrane to the solid matrix in a lateral direction. The filtration membrane has a sample application zone (210) and a transfer zone (212). Filtration membrane is in direct contact with the solid matrix via the transfer zone. Essentially, the transfer zone of the filtration membrane is the part of the filtration membrane that touches the dry solid matrix when the filtration membrane is in direct contact with the solid matrix. The sample application zone is used for receiving biological sample and the transfer zone is used for delivering non-cellular fraction of biological sample to the dry solid matrix. In some embodiments, the filtration membrane and dry solid matrix are arranged such that they may partially overlap each other. In other embodiments, the filtration membrane and dry solid matrix are arranged such that they may not overlap each other but still biological sample passes through the filtration membrane to the solid matrix in the lateral direction. In such case, the dry solid matrix is positioned downstream of the filtration membrane, touching the filtration membrane but not overlapping. In some embodiments, the filtration membrane is disposed on a first solid support (206) and the dry solid matrix is disposed on a second solid support (208). In some embodiments, the first solid support and the second solid support are arranged facing opposite to each other. In other embodiments, the first solid support and the second solid support may be arranged next to each other. In some embodiments, the filtration membrane and dry solid matrix are laterally disposed on a solid support (206). In some embodiments, a second solid support (208) is included over the dry solid matrix to sandwich the dry solid matrix against the filtration membrane and establish an effective transfer zone, for example, as in FIG. 2.

Figure 3:
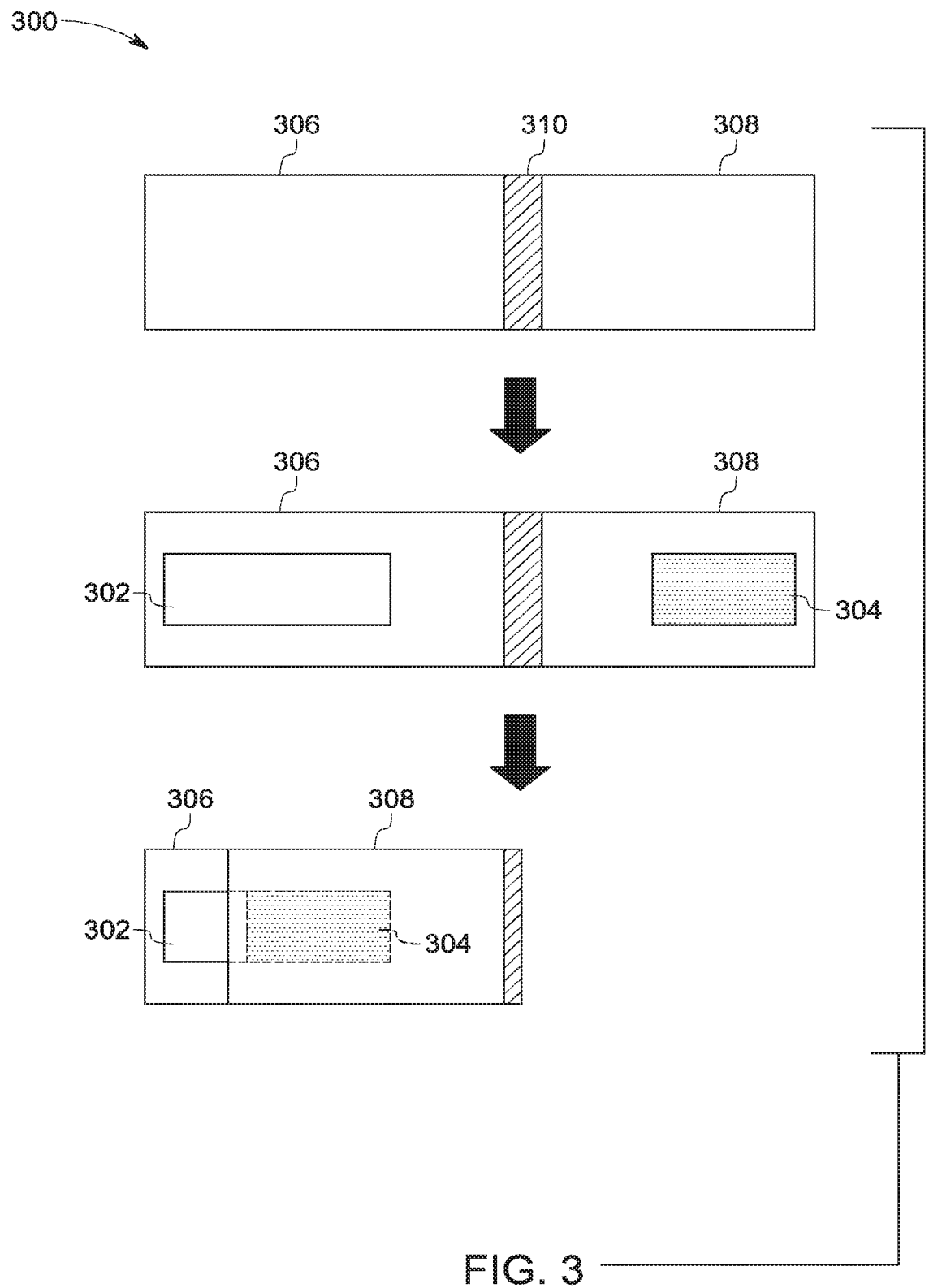
FIG. 3 depicts a schematic representation of an embodiment for making the lateral flow device for the separation and collection of non-cellular fraction of a biological sample.

The first solid support may be connected to the second solid support via a means for establishing a direct contract of the filtration membrane with the dry solid matrix. The means for establishing direct contact may be a hinge, foldable indentation, or an otherwise pliable connection. In some embodiments, the lateral flow device may be configured by a process (300) as shown in FIG. 3. The first solid support (306) and the second solid support (308) are connected to each other via a foldable hinge (310). The first solid support has a filtration membrane (302) disposed on it and the second solid support has a dry solid matrix (304) disposed on it. The filtration membrane may be brought in direct contact with the dry solid matrix by folding the hinge such that the filtration membrane and the dry solid matrix partially overlap each other. In one embodiment, the lateral flow device comprises an MF1™ filtration membrane and a cellulose-based dry solid matrix. In embodiments where plasma/serum is collected from whole blood, whole blood is applied and passed across the filtration membrane, and non-cellular plasma or serum is collected or wicked on to the dry solid matrix.

Figure 4:
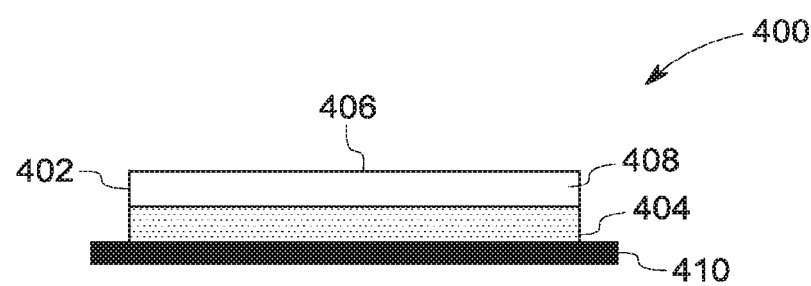
FIG. 4 depicts a schematic representation of a vertical flow device for the separation and collection of non-cellular fraction of a biological sample.

In some embodiments, the device may be a vertical flow device. A schematic representation of the vertical flow device (400) is illustrated in FIG. 4. The device (400) contains the filtration membrane (402) and the dry solid matrix (404), wherein the filtration membrane is disposed on to the dry solid matrix. The filtration membrane is in direct contact with the solid matrix. The filtration membrane has a sample application zone (406) and a transfer zone (408). The sample application zone is used for receiving biological sample and the transfer zone is used for delivering a filtered non-cellular fraction of the biological sample to the dry solid matrix. The transfer zone of the filtration membrane is defined by a zone which is in touch with the dry solid matrix. As shown, the filtration membrane and the dry solid matrix are arranged such that non-cellular fraction of the biological sample can pass through the filtration membrane to the solid matrix in a vertical direction. In some embodiments, the dry solid matrix is disposed on to a third solid support (410). In one embodiment, the vertical flow device comprises a Vivid™ or Primecare™ filtration membrane and a cellulose-based dry solid matrix. In the embodiments where plasma/serum is collected from whole blood, whole blood is applied and passed through the filtration membrane, and non-cellular plasma or serum is collected or wicked on to the dry solid matrix.

As described above, a first solid support may carry the filtration membrane and a second and third solid support may carry the dry solid matrix. The solid support may be positioned directly adjacent to the filtration membrane or dry solid matrix membrane as shown in FIG. 2, FIG. 3 or FIG. 4. In some embodiments, one or more intervening layers may be positioned between the solid support and the filtration membrane and/or the dry solid matrix. The solid support may be formed from any material that is able to carry the filtration membrane and/or dry solid matrix. The support may be formed from a material that is transmissive to light, such as transparent or optically diffuse (e.g., transluscent) materials. It may be desirable that the solid support is liquid-impermeable so that the fluid flowing through the membrane or solid matrix does not leak through the solid support. Examples of suitable materials for the solid support include, but are not limited to, glass, polymeric materials such as polystyrene, polypropylene, polyester, polybutadiene, polyvinylchloride, polyamide, polycarbonate, epoxides, methacrylates or polymelamine. To provide a sufficient structural backing for the membrane or solid matrix, the solid support is generally selected to have a certain minimum thickness. For example, the solid support may have a thickness that ranges from about 1/16 inch to about 1/4 inch. In one embodiment, the solid support is polycarbonate-based (Clear Lexan™) having a thickness of about 0.10 inch.

Detergents may precipitate out of solution while employing the nucleic acid precipitation methods described above and therefore would interfere with the method of nucleic acid preparation and analysis. Therefore, the dry solid matrix of the device described herein is devoid of any detergent such as sodium dodecyl sulfate (SDS), SLS (lauryl), alkyl aryl sulfonates, long chain alcohol sulfates, olefin sulfates, sulfosuccinates, phosphate esters, sodium 2-ethylhexysulfate, polyvinyl sulfate, polyacrylate, polyphosphate, sodium polyacrylate or sodium polyvinyl sulfate. In some embodiments, the dry solid matrix may be impregnated with a chaotropic salt.

In some embodiments, the device is designed such that the dry solid matrix is well suited for direct downstream analysis (e.g. nucleic acid extraction) without any further processing such as coring or punching. In particular, the dry solid matrix of the device has a dimension which makes it suitable to fit entirely into standard laboratory extraction vessels (e.g., microcentrifuge tube, centrifuge tubes). In one embodiment, the dimensional width of the dry solid matrix is up to about 8 millimeters so that it fits entirely inside an extraction vessel. Such device design aids in eliminating the requirement for coring or punching the material prior to sample extraction, and therefore minimizes DNA contamination from the surrounding sample environment that might feed into whole genome amplification.

In some embodiments, the filtration membrane is also scaled proportionally to a maximum dimensional width of 8 mm in order to establish even sample wicking with the solid matrix. The dimensional lengths of the filtration membrane and solid matrix are dictated by the desired input volume of the biological sample. In one embodiment, for lateral flow separation of 100 µL whole blood, the optimal dimension of the MF1™ filtration membrane is 8 mm wide×20 mm long. At this dimension, the red blood cell front arrests near the interface of the solid matrix, thereby minimizing the volume of plasma retained on the filtration membrane and maximizing transfer of the plasma onto the dry solid matrix. For vertical flow separation of 100 µL whole blood, the optimal dimension of Vivid™ or Primecare™ filtration membrane is 8 mm wide×32 mm long.

In some embodiments, the solid matrix may be decoupled from the upstream filtration membrane and stored at ambient temperature for long-term archiving after sample filtration and transfer of non-cellular fraction onto the solid matrix. Furthermore, the non-cellular fraction that is transferred to the dry solid matrix may be dried so that it can be stored for longer periods without damaging the circulating nucleic acids present therein. At the time of analysis, circulating nucleic acid can be extracted from the solid matrix by transferring the solid matrix into a conventional extraction vessel (e.g. a microcentrifuge tube) and rehydrating the matrix in a suitable extraction buffer.

The device as described above may be used for collecting a non-cellular fraction of a biological sample at the point-of-collection of said biological sample. Biological sample may be provided directly on the filtration membrane without any pre-treatment at the point of sample collection. Once the filtration step is complete, a non-cellular fraction may be collected on to the dry solid matrix and stored. In some embodiments, a method for collecting plasma or serum from whole blood using the device is described. The method comprises the steps of providing the whole blood at the sample application zone of the filtration membrane, allowing the whole blood to pass through the filtration membrane to separate the plasma or serum from blood cells, and collecting the separated plasma or serum on the dry solid matrix. Once collected, the plasma or serum may be dried on the solid matrix for long term storage. The entire process may be done at the point-of-collect of the whole blood sample. Later on, the dried plasma or serum fraction having circulating nucleic acids may be further processed by the methods described herein for downstream analysis. In some embodiments, less than 100 µL of whole blood sample may be used to collect plasma or serum.

The device presented herein may further include additional functional components that do not affect the basic functionality of the device, namely the collection of a non-cellular fraction having circulating nucleic acids from the biological sample. For example, additional filtration membranes with different pore size may be included in the device. In some embodiments, the device includes a single filtration membrane configured to separate a non-cellular fraction from intact cells and a single dry solid matrix configured to collect the separated non-cellular fraction. In some other embodiments, the device may include a filtration membrane configured to separate a non-cellular fraction from intact cells, a dry solid matrix configured to collect the separated non-cellular fraction, and other functional components that do not alter the basic functionality of the device. Examples of such other functional components include, but not limited to, a solid support, casing for the device, holding rings and/or covering membranes.

Practice of the invention will be still more fully understood from the following examples, which are presented herein for illustration only and should not be construed as limiting the scope of the present invention as defined by the appended claims. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "µL": microliters; "min.": minutes and "h.": hours.

EXAMPLES

Example 1

Figure 5:
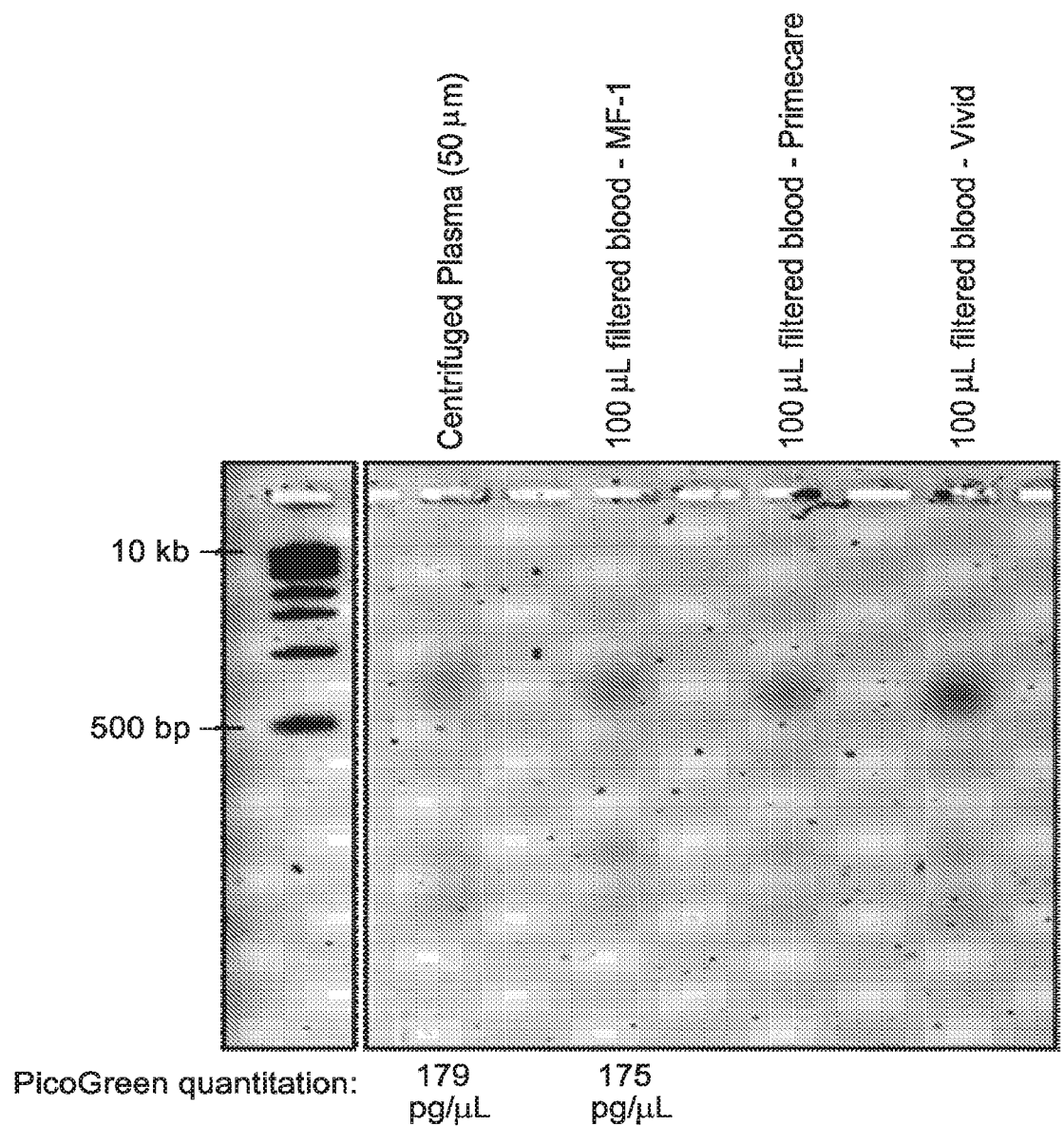
FIG. 5 depicts plasma DNA collection on to a dry solid matrix following lateral or vertical separation of human whole blood.

Circulating DNA Collection on Plasma Collection Membranes Following Lateral or Vertical Separation of Human Whole Blood For lateral flow devices, MF1™ membrane was used as a filtration membrane and 903 cellulose paper was used as a dry solid matrix. For vertical flow devices, Primecare™ and Vivid™ membranes were used as filtration membranes and 903 cellulose paper was used as a dry solid matrix. 100 μL of human whole blood was applied on to the filtration membranes of the lateral or vertical flow devices and plasma was collected on to the dry solid matrix. The collected plasma was placed into a desiccator cabinet and dried at room temperature to form a dried plasma sample. Following 24 hours of storage, plasma DNA was extracted from each solid matrix by adaptation of DNA Extractor SP (Wako Chemical), and precipitated plasma DNA was analyzed using gel electrophoresis. For comparative purposes, whole blood was centrifuged with three-step gentle protocol (1600×g, 10 minutes; collect and re-spin plasma at 1600×g, 10 minutes; collect and spin at 16,000×g, 10 minutes for cell-free plasma), and 50 μL of centrifuged plasma was spotted onto identical 903 cellulose paper, extracted, and analyzed in parallel. FIG. 5 demonstrates that circulating plasma DNA is efficiently collected and stabilized from a dry solid matrix overlapped downstream of commercially-available filtration membranes. The yield of plasma-circulating DNA was measured with a PicoGreen assay and demonstrated similar DNA recovery between MF1-filtered whole blood (175 μg/μL) and centrifuged plasma (179 μg/μL). In contrast, a small amount of genomic contamination (DNA>10 kB) was visible following filtration using Primecare™ and Vivid membranes (vertical flow filtration). However, no genomic contamination was seen after MF1 lateral-flow filtration or gentle centrifugation.

Example 2

Figure 6:
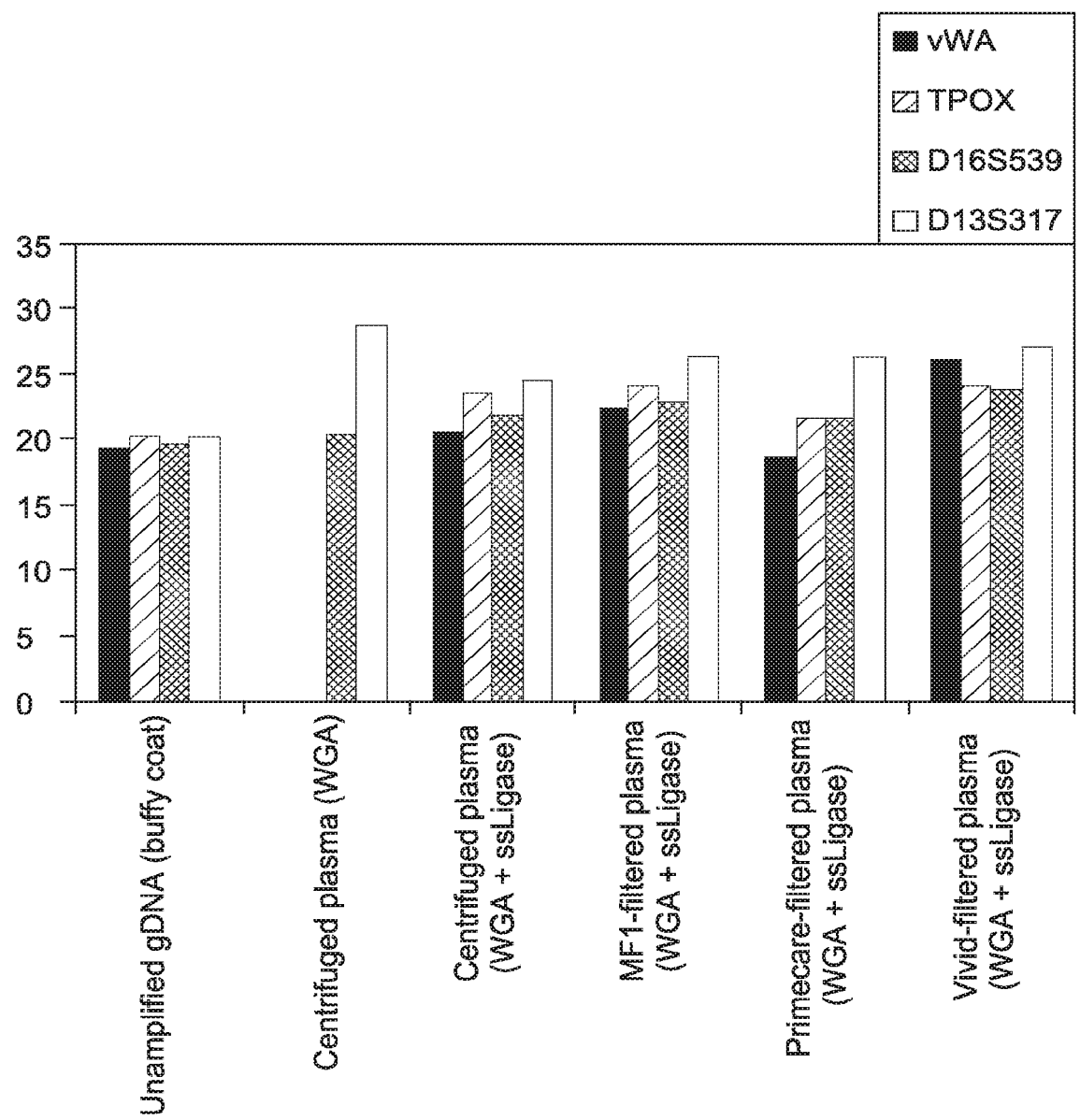
FIG. 6 depicts ligase-assisted whole genome amplification that enables detection of four different chromosomal loci from plasma DNA (i.e., circulating DNA extracted from plasma) separated from whole blood by lateral or vertical flow.

Ligase-Assisted Whole Genome Amplification for Detection of Four Different Chromosomal Loci from Plasma DNA Separated from Whole Blood by Lateral or Vertical Flow Plasma DNA extracted from the dry solid matrix (903 cellulose paper) from Example 1 was amplified using rolling circle amplification techniques in the absence or presence of a commercial single strand-specific ligase (CircLigase, Epi-Centre), and four random STR chromosomal loci (vWA, TPDX, D8S1129, and D13S317) were interrogated to assess genomic coverage. FIG. 6 demonstrates that rolling circle amplification techniques combined with single-strand-specific ligase activity enables sensitive detection of all four chromosomal STR loci from picogram quantities of plasma-circulating DNA. The experiment was performed using mini-STR primer sets, since traditional STR primer pairs typical amplify regions of DNA that are larger than circulating DNA itself. Single-strand-specific ligase activity in combination with rolling circle amplification technique permitted detection of plasma STR loci with qPCR CT values close to that of unamplified genomic DNA from buffy coat fractions, which were isolated by centrifugation and extracted using QIAamp DNA blood mini kit (Qiagen) (FIG. 6). Without single-strand-specific ligase activity, only two out of four plasma STR markers could be detected using the rolling circle amplification technique alone. Using ligase-assisted whole genome amplification, STR detection levels from plasma appeared similar between membrane-filtered blood and centrifuged blood.

Example 3

Whole-Genome Amplification of Circulating Nucleic Acid from Blood Plasma

Figure 8:
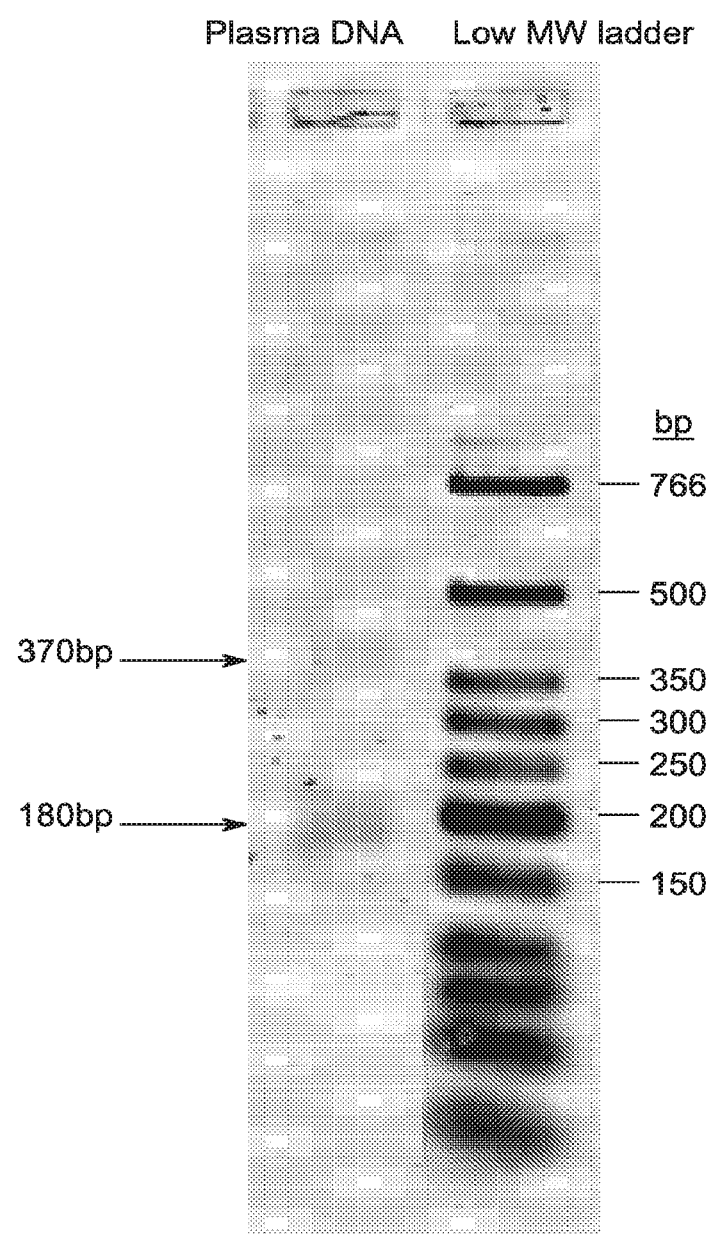
FIG. 8 illustrates the size profiles of circulating DNA isolated from blood plasma of healthy individuals.

Circulating DNA was isolated from citrate-phosphate-dextrose (CPD)—stabilized blood plasma of apparently healthy individuals using the Wako DNA extractor SP kit (Wako Pure Chemical Industries). Approximately 1.3 ng was analyzed by electrophoresis through a 2% agarose gel using TBE buffer, stained with SYBR Gold and visualized using a Typhoon imager. As depicted in FIG. 8, the majority of the circulating DNA was approximately 180 bp in length, with an additional smaller amount of sequences that were approximately 370 bp long, and a substantially smaller amount of higher molecular weight sequences.

350 pg circulating DNA from plasma was heated at 95° C. to denature the template. The denatured, single-stranded DNA template was then treated with an RNA or DNA ligase to generated single-stranded DNA circles. ATP-dependent T4 DNA ligase, cell-encoded NAD-dependent *E. coli* DNA ligase or a thermostable RNA ligase (CircLigase II) were used for these ligation reactions. 100 pg of ligated single-stranded DNA circles were then subjected to whole-genome amplification using GenomiPhi kit (GE Healthcare) employing a Phi29 DNA polymerase. The amplification was performed using the primer mixture +N+N(at N)(at N)(at N)*N where +N represents an LNA nucleotide and "at N" represents a random mixture containing 2-amino dA, 2-thio dT, normal G and normal C. Real time amplification, wherein the amplification and quantification of the target nucleic acid is done simultaneously, was performed by adding a small amount of SYBR green I to the amplification mixture and monitoring the fluorescence signal increase over time in a Tecan plate reader (Tecan Sniper, Amersham Pharmecia Biotech). For comparison, an equivalent concentration of untreated genomic DNA, untreated plasma DNA, and a sample without DNA template (No template amplification) were included.

Figure 9A:
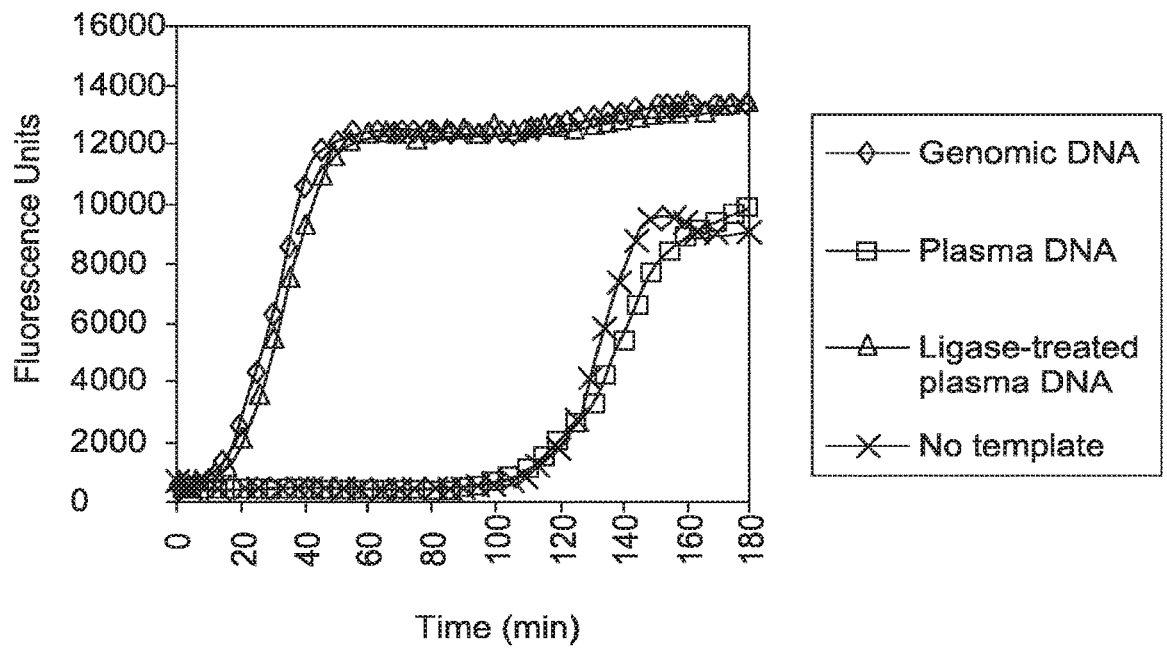
FIGS. 9A, 9B and 9C illustrate ligase-assisted whole-genome amplifications of circulating DNA extracted from the non-cellular fraction of whole blood, using different ligases.
Figure 9B:
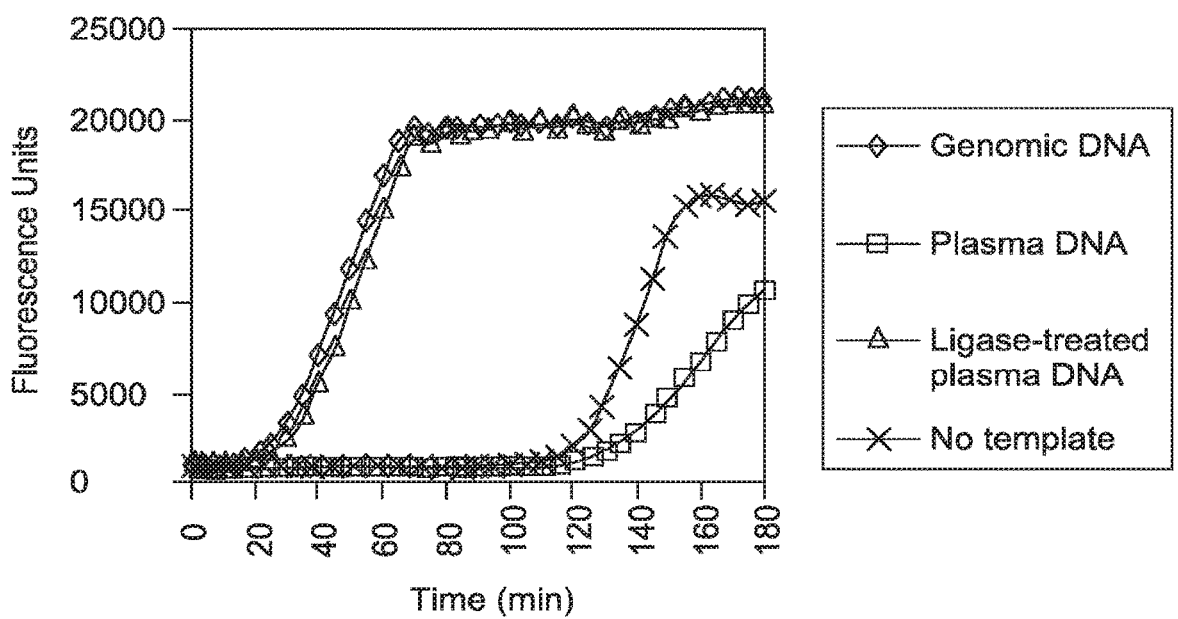
Figure 9C:
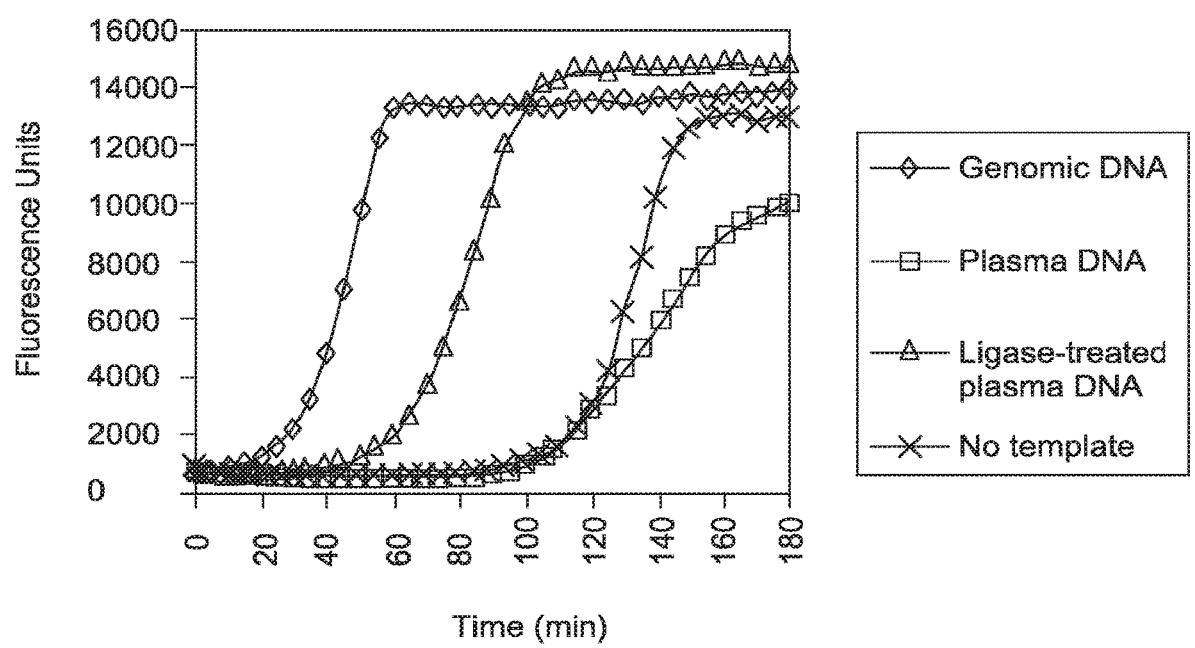

As depicted in FIG. 9, the amplification kinetics of the untreated, fragmented plasma DNA was much lower when compared with an equivalent amount of high molecular weight genomic DNA, indicating a defect in amplification. However, when the fragmented plasma DNA was pre-treated and converted to single-stranded DNA circles using the CircLigase™ II, rapid amplification kinetics was achieved (FIG. 9A). Other ligases, including the ATP-dependent T4 DNA ligase (FIG. 9B) and the cell-encoded NAD-dependent *E. coli* DNA ligase (FIG. 9C) were also effective in restoring amplification kinetics of the fragmented plasma DNA. In these examples, the relative increase in amplification kinetics indicates the effectiveness of each of the ligases in promoting the intra-molecular ligation of the single-stranded DNA template.

Example 4

Figure 10:
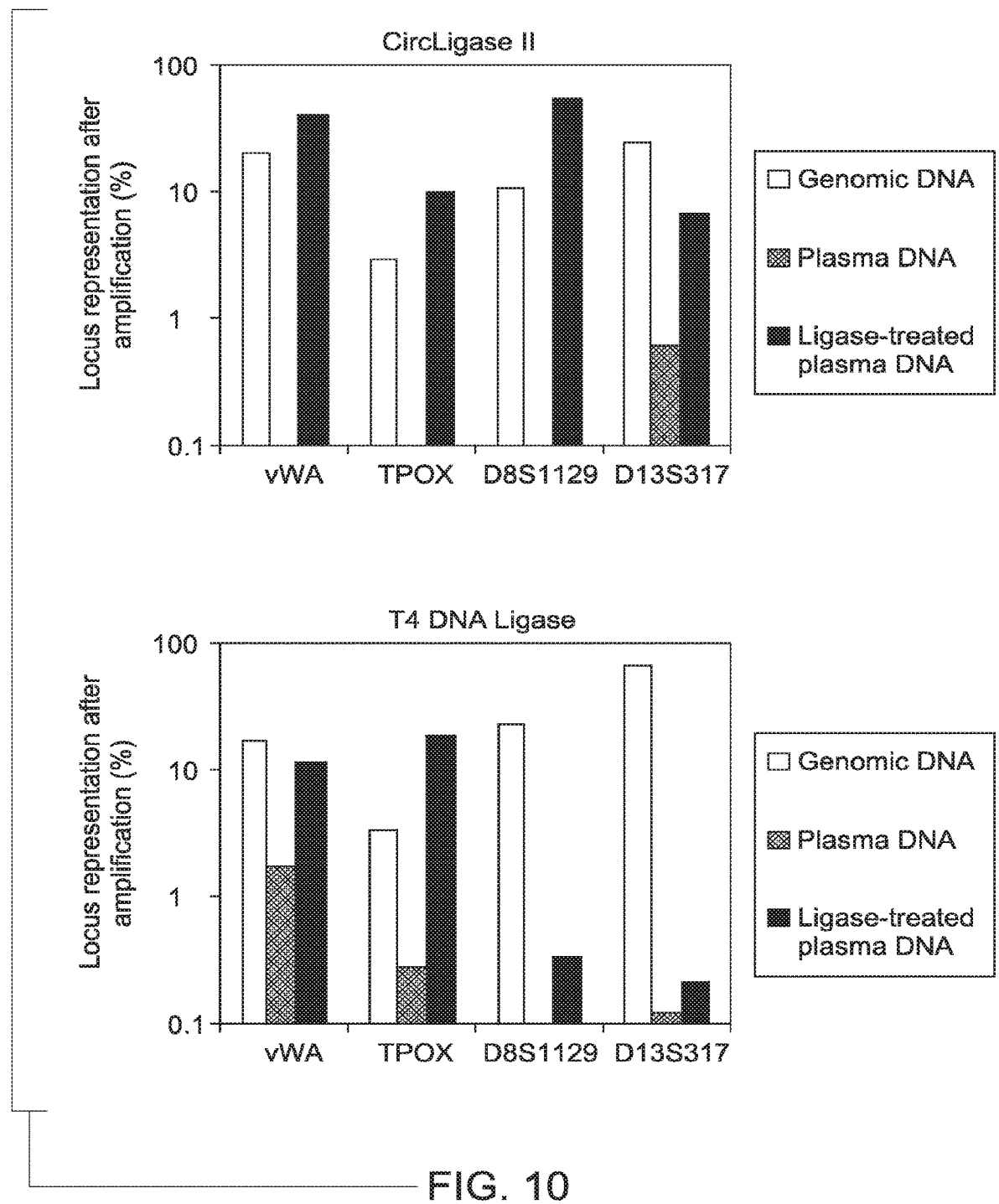
FIG. 10 illustrates the effectiveness of ligase-assisted whole-genome amplification for sensitive and balanced DNA amplification of four different CODIS loci.

Analysis of Amplified Circulating Nucleic Acids from Blood Plasma by Ligase-Assisted Whole-Genome Amplification The amplified DNA generated in Example 3 was further analyzed by quantitative PCR using primers targeting four different CODIS loci (vWA, TPDX, D8S1129, and D13S317) in order to sample the effectiveness of the ligase-assisted whole-genome amplification method for promoting sensitive and balanced DNA amplification. These DNA levels were compared with the values from unamplified DNA to determine the relative representation levels after amplification. As illustrated in FIG. 10, in both examples, qPCR analysis of untreated plasma DNA led to sequence dropout or produced DNA that was highly under-represented at the tested loci. In contrast, including either CircLigase™ II or T4 DNA ligase in the method prevented the sequence dropout of the four loci and produced DNA that was more similar in representation to the amplified high molecular weight genomic DNA. In a further example using CircLigase™ II as the single-stranded DNA ligase, out of 12 different CODIS loci tested by quantitative PCR (qPCR), 11 were detected after ligase-assisted whole genome amplification, whereas only 4 were present in the untreated plasma DNA (FIG. 11). In FIG. 11, the Ct values reported are an average of two replicates. PCR reactions where the Ct value was undetermined are marked by an "X".

Example 5

Optimization of Reaction Conditions for Ligase-Assisted Whole-Genome Amplification The ligase-assisted DNA amplification reaction was further optimized by optimizing the efficiency of ligation reaction of single-stranded DNA molecules by TS2126 RNA ligase. The presence of metal ion was essential for the ligation reaction since eliminating manganese from the standard manufacturer-recommended buffer reduced amplification rates to background levels. Untreated genomic DNA and untreated plasma DNA were compared with CircLigase II™-treated plasma DNA samples using modified buffer conditions. All buffer conditions contained 33 mM KoAc, 0.5 mM DTT, and 1 M betaine. Where indicated, the buffers contained 33 mM Tris-acetate (pH 7.5) or 33 mM HEPES-KOH (pH 8.0) and additionally contained 2.5 mM $MgCl_2$ or 2.5 mM $MnCl_2$. Real time amplification was performed by adding a small amount of SYBR green I to the amplification mixture and monitoring fluorescence increase over time in a Tecan plate reader. Amplification threshold is the time at which fluorescence rises above background levels (2000 RFU).

Figure 12:
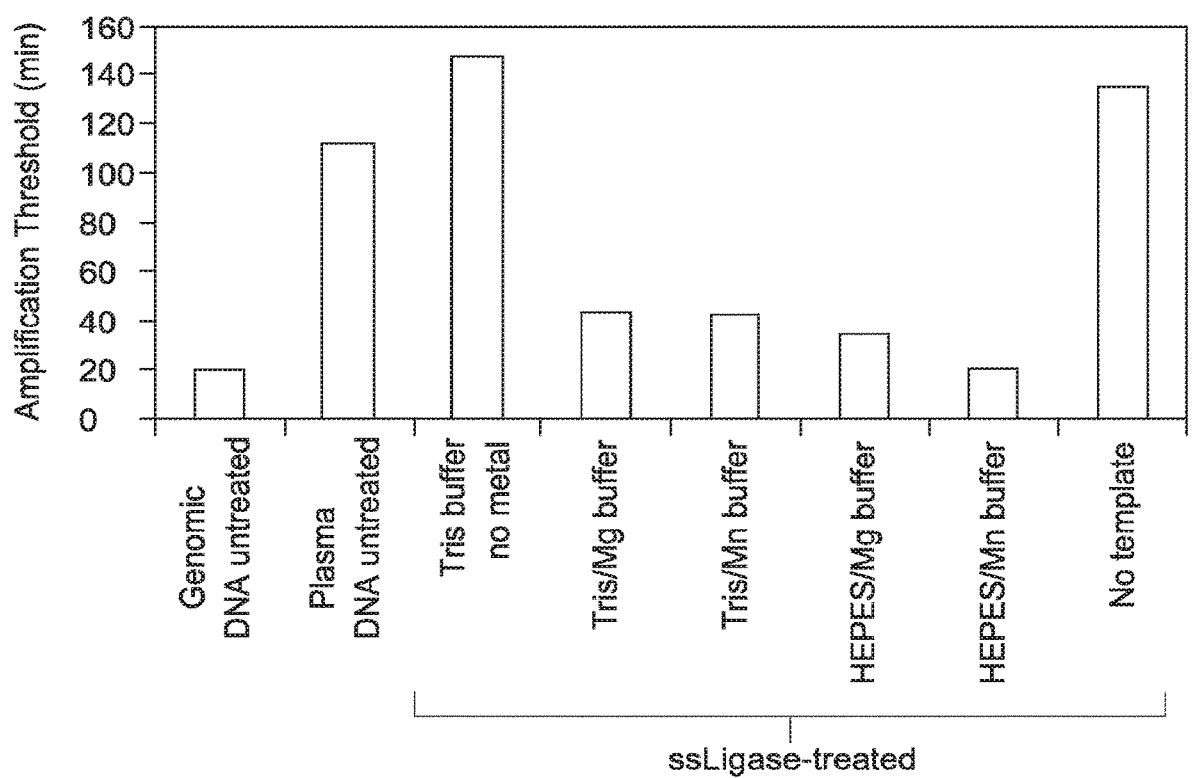
FIG. 12 illustrates the varying efficiencies of ligase-assisted whole-genome amplification in different reaction and buffer conditions.

A comparison of amplification kinetics of ligase-assisted whole-genome amplification reactions (100 pg input of circulating DNA) is depicted in FIG. 12. Both magnesium and manganese produced similar effects in the presence of the standard TRIS buffer. However, a combination of manganese and magnesium in the presence of HEPES buffer, pH 8.0 promoted higher amplification rates. HEPES buffer increased circularization efficiency of the plasma DNA in these reactions by decreasing the oxidation rate of the manganese cations compared to TRIS buffer.

Example 6

Inhibition of Amplification of High Molecule Weight Genomic DNA in Ligase-Assisted Whole-Genome Amplification The amplification kinetics of whole-genome amplification of untreated genomic DNA was compared to CircLigase™ I and CircLigase™ II-treated genomic DNA samples (100 pg DNA input). The results are illustrated in FIG. 13. As depicted in FIG. 13, CircLigase™ treatment of single-stranded genomic DNA produced an inhibitory effect on the amplification rate of high molecular weight genomic DNA (unlike the positive effects on plasma DNA such as illustrated in FIG. 9A). The inhibition was apparent for both CircLigase™ I and CircLigase™ II.

To investigate if Phi29-based amplification was inhibited by the ligase, untreated double-stranded genomic DNA was amplified in the presence of active ligase. Real time amplification was performed by adding a small amount of SYBR green I to the amplification mixture and monitoring fluorescence increase over time in a Tecan plate reader. Amplification threshold is the time at which fluorescence rises above background levels (2000 RFU). It was observed that the genomic DNA amplification inhibition was not a consequence of active ligase being present during the amplification.

A preference for the amplification of circulating over high molecular weight genomic DNA might be an advantage for certain applications, as genomic DNA from blood cells often contaminates preparations of circulating nucleic acids, and is of less diagnostic value.

Example 7

Single-tube Amplification of Fragmented DNA Employing Ligase-Assisted Whole-Genome Amplification—Effect of Phosphorylation of Circulating DNA Fragments with Kinase Prior to Intra-Molecular Ligation Phosphorylation of circulating DNA fragments with kinase was discovered to elicit more sensitive detection of circulating DNA in blood plasma. A male-female plasma/blood mixing experiment demonstrated that the DNA library created from input CNA treated with kinase was more representative, allowing for more sensitive detection of the DYS14 male-specific marker (3/3 replicates, whereas only 1/3 was detected if phosphorylation was not done). 100 uL of blood/plasma mixtures were prepared as follows: 100A: 100% male plasma; 5A-C: male plasma spiked into female whole blood at 5% v/v; 1A-C: male plasma spiked into female whole blood at 1% v/v; and 0A: 100% female blood. The plasma was separated from the blood cells by lateral flow through an MF1 membrane followed by collection onto a 903 cellulose pad, which was subsequently dried and stored overnight. Circulating DNA was then extracted from the cellulose pad by a modification of the Wako extractor SP kit (Wako Pure Chemical Industries), a standard sodium iodide/detergent based method. Approximately 1.8 ng of DNA was then treated with or without T4 polynucleotide kinase in the presence of GTP, manganese, and betaine and then treated with CircLigase II™ to circularize the single-stranded DNA fragments. DNA was then subjected to GenomiPhi whole-genome amplification (GE Healthcare) and products were analyzed by quantitative PCR to assess the detection of two markers: Dys14, which is a multi-copy gene located on the Y-chromosome and should be detectible from the male fraction only, and D16S539 which is an STR locus located on chromosome 16 and should be detectible from both male and female fractions. The reaction was performed in a single reaction vessel, without any intermediate purification or isolation steps in the workflow. This was achieved by performing the phosphorylation reaction at a relatively low concentration of GTP.

Figure 14:
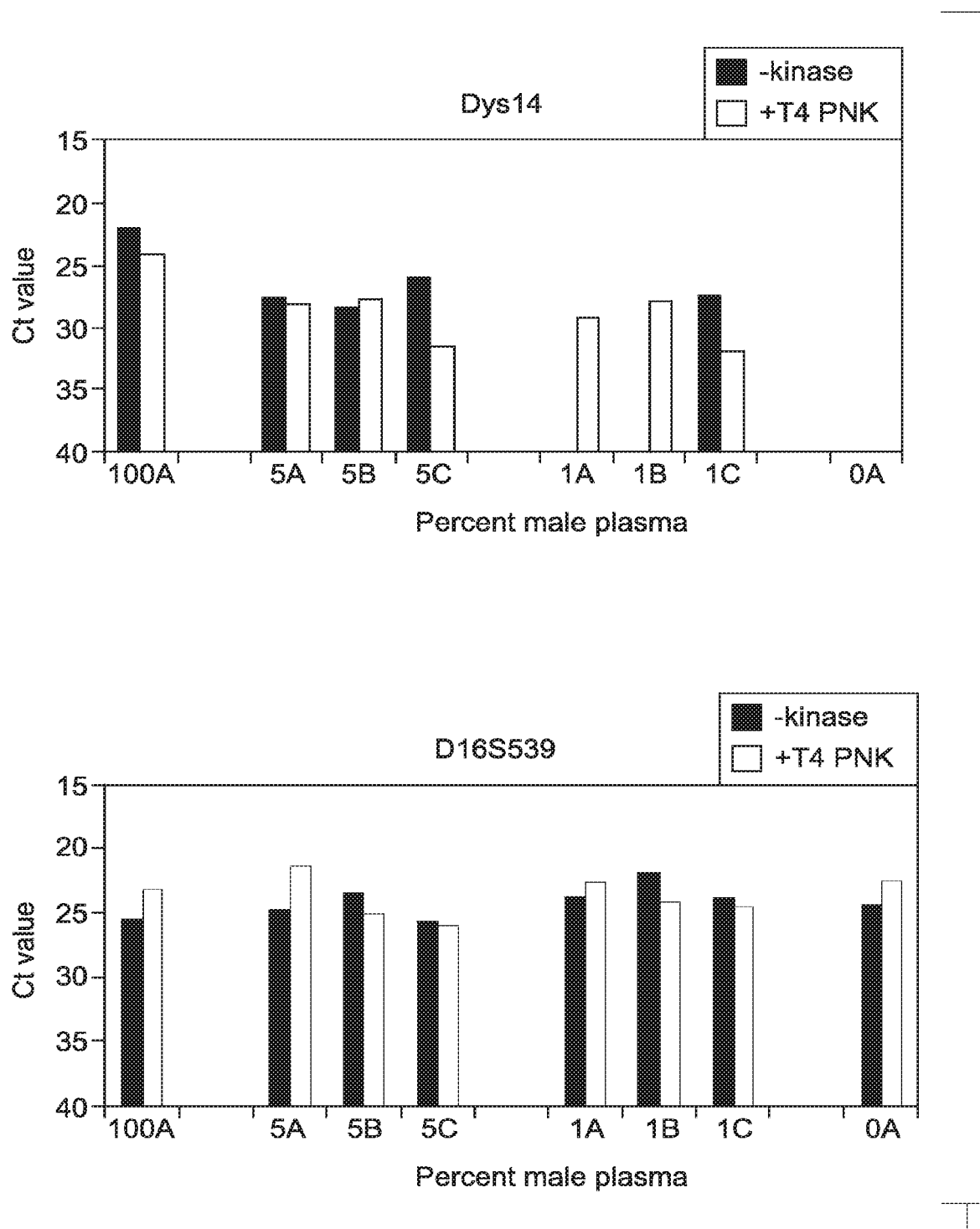
FIG. 14 illustrates a single-tube ligase-assisted amplification reaction using male-female plasma/blood, wherein DYS14 male-specific marker is detected using a library created from the input CNA.

FIG. 14 illustrates that inclusion of a kinase in the reaction allows for circularization and amplification of CNA fragments that do not necessarily contain a 5' phosphate, thereby creating a more representative library. This would include DNA fragments containing a 5' hydroxyl, which are specifically generated by DNase II digestion during cell death. Using a male-female plasma/blood mixing experiment, it is demonstrated that the library created from the input DNA treated with kinase is more representative, allowing for more sensitive detection of the DYS14 male-specific marker (3/3 replicates, whereas only 1/3 was detected if phosphorylation was not done).

The claimed invention may be embodied in other specific forms without departing from the spirit or essential characteristics thereof. The foregoing embodiments are selected embodiments or examples from a manifold of all possible embodiments or examples. The foregoing embodiments are therefore to be considered in all respects as illustrative rather than limiting on the invention described herein. While only certain features of the claimed invention have been illustrated and described herein, it is to be understood that one skilled in the art, given the benefit of this disclosure, will be able to identify, select, optimize or modify suitable conditions/parameters for using the methods in accordance with the principles of the present invention, suitable for these and other types of applications. The precise use, choice of reagents, choice of variables such as concentration, volume, incubation time, incubation temperature, and the like may depend in large part on the particular application for which it is intended. It is, therefore, to be understood that the appended claims are intended to cover all modifications and changes that fall within the true spirit of the invention. Further, all changes that come within the meaning and range of equivalency of the claims are intended to be embraced therein.

The invention claimed is:

1. A method for processing a whole blood sample at a point of sample collection to collect circulating nucleic acid in plasma or serum, the method comprising:
    a) applying the whole blood sample directly on to a filtration membrane at the point of sample collection;
    b) separating, at the point of sample collection, the non-cellular fraction by filtering the whole blood sample through the filtration membrane in the absence of an anti-coagulant, wherein the intact cells in the whole blood are retained on the filtration membrane, and wherein the non-cellular fraction comprises plasma or serum;
    c) collecting the separated non-cellular fraction onto a dry solid matrix, wherein the dry solid matrix is configured to establish a direct contact with the filtration membrane, wherein the dry solid matrix comprises cellulose and wherein the dry solid matrix is devoid of any detergent lysis buffer;
    d) drying the collected non-cellular fraction on the solid matrix; and
    e) storing the dry solid matrix containing the collected circulating nucleic acids in the non-cellular fraction.

2. The method of claim 1, wherein the separating step is performed using vertical flow.

3. The method of claim 1, wherein the separating step is performed using lateral flow.

4. The method of claim 1, wherein the filtration membrane comprises pores with a diameter of less than or equal to about 5 microns.

5. The method of claim 1, wherein the drying occurs under ambient conditions or by vacuum-assisted evaporations.

6. The method of claim 1, wherein the whole blood sample comprises a circulating nucleic acid.

7. The method of claim 6, wherein the circulating nucleic acid is derived from a tumor, a fetus, a donated organ after implantation, a transplanted cell, a transplanted tissue, or a diseased state.

8. The method of claim 6, wherein the circulating nucleic acid is a circulating DNA or a circulating RNA, wherein the circulating DNA comprises a tumor-derived DNA, a fetus-derived DNA, a donated organ-derived DNA, a transplanted cell-derived DNA, a transplanted tissue-derived DNA, or a combination thereof.

9. The method of claim 1, wherein the dried, collected non-cellular fraction is stored on the dry solid matrix for at least 30 minutes.

10. The method of claim 1, wherein the dried, collected non-cellular fraction is stored on the dry solid matrix under dry or desiccated conditions or under inert atmospheres.

11. The method of claim 6, wherein the circulating nucleic acid is stabilized for at least 24 hours at ambient conditions.

12. The method of claim 1, wherein an intervening layer is positioned between the filtration membrane and the dry solid matrix.

13. The method of claim 1, wherein the filtration membrane and the dry solid matrix are fully overlapping.

14. The method of claim 1, wherein the filtration membrane and the dry solid matrix are partially overlapping.

15. The method of claim 1, wherein the dry solid matrix comprises a cellulose paper.

16. The method of claim 1, wherein the dry solid matrix is impregnated with a chaotropic salt.

17. The method of claim 16, wherein the chaotropic salt is selected from a group consisting of: guanidine thiocyanate, guanidine chloride, guanidine hydrochloride, guanidine isothiocyanate, sodium thiocyanate, and sodium iodide.

18. The method of claim 1, wherein a volume of whole blood sample applied to the filtration membrane is about 10 µL to about 500 µL.

19. The method of claim 1, wherein the filtering step is performed without a prior pre-treatment of the whole blood.

20. The method of claim 1, further comprising:
    f) amplifying the collected circulating nucleic acids using random primers comprising a nucleotide analogue in a single reaction vessel; and
    g) detecting a presence, absence, or quantity of a specific circulating nucleic acid sequence in the amplified circulating nucleic acid product.

* * * * *